US008715986B2

(12) United States Patent
Gonzalez

(10) Patent No.: US 8,715,986 B2
(45) Date of Patent: May 6, 2014

(54) STEREOISOMER PEPTIDES, LIGAND-TARGETED MULTI-STEREOISOMER PEPTIDE POLYMER CONJUGATES, AND USES THEREOF

(76) Inventor: Lucia Irene Gonzalez, Baltimore, MD (US)

( * ) Notice: Subject to any disclaimer, the term of this patent is extended or adjusted under 35 U.S.C. 154(b) by 487 days.

(21) Appl. No.: 12/914,050

(22) Filed: Oct. 28, 2010

(65) Prior Publication Data
US 2011/0104783 A1 May 5, 2011

Related U.S. Application Data

(60) Provisional application No. 61/256,260, filed on Oct. 29, 2009.

(51) Int. Cl.
| C12N 9/96 | (2006.01) |
| A61K 38/00 | (2006.01) |
| C07K 1/00 | (2006.01) |
| C07K 14/00 | (2006.01) |
| C07K 17/00 | (2006.01) |
| A61K 38/24 | (2006.01) |
| A61K 38/27 | (2006.01) |
| C07K 16/00 | (2006.01) |
| C08H 1/00 | (2006.01) |

(52) U.S. Cl.
USPC ........... 435/188; 530/345; 530/402; 530/351; 530/399

(58) Field of Classification Search
None
See application file for complete search history.

(56) References Cited

U.S. PATENT DOCUMENTS

| 6,440,461 B1 | 8/2002 | Bru-Magniez et al. |
| 7,141,540 B2 | 11/2006 | Wang et al. |
| 7,332,523 B2 | 2/2008 | Satchi-Fainaro et al. |
| 7,569,222 B2 | 8/2009 | Woerly |
| 7,662,360 B2 | 2/2010 | Patel |

FOREIGN PATENT DOCUMENTS

| WO | WO9733618 | 9/1997 |
| WO | WO03066068 | 8/2003 |

OTHER PUBLICATIONS

Shamay et al "E-selectin binding peptide-polymer-drug conjugates and their selective cytotoxicity against vascular endothelial cells" Biomaterials 30:6460-6468. Published online Aug. 28, 2009.*

(Continued)

Primary Examiner — Cecilia J Tsang
Assistant Examiner — Zachary J Miknis

(57) ABSTRACT

The invention provides compounds of the formula Poly-([SP-LI]n-PL-L2) including a collection of 152 peptides useful to create the compounds, and their uses thereof for the treatment of a variety of mammalian diseases. The compound, a novel ligand-targeted multi-stereoisomer peptide polymer conjugate, comprises two or more stereoisomer peptides and a peptide-ligand conjugated via linkers to a biocompatible hydrophilic polymer, preferably HPMA. The increased stability and solubility of the compound carrying the stereoisomer peptides and a peptide-ligand provide ideal pharmaceutical properties including the delivery by the polymer of the peptides into the target cells. The compounds of the invention are useful therapeutics for the treatment of a variety of mammalian diseases. Examples of such diseases in human patients include abnormal angiogenesis, pathological conditions of the eye, cancer, metastasis, diabetes, Alzheimer's and Parkinson's diseases, brain and neurodegenerative disorders, bipolar disorder, and diseases caused by aging and pathogen agents, to name a few.

5 Claims, 1 Drawing Sheet

(56) References Cited

OTHER PUBLICATIONS

Kopecek J and Kopeckova P "HPMA copolymers: Origins, early developments, present, and future" Adv Drug Deliv Rev 62:122-149. Published online Nov. 14, 2009.*

Nori A "Design, Synthesis and Evaluation of HPMA Copolymer—Tat Conjugates as Potential Carriers for Drug Delivery" Doctoral Dissertation, The University of Utah. Published May 2009.*

Maeda et al. "Conjugates of Anticancer Agents and Polymers: Advantages of Macromolecular Therapeutics in Vivo", 1992, 3(5):351-362.

Greco et al. "Polymer-drug Conjugates: Current Status and Future Trends", 2008, Front. Biosci. 13, 2744-2756.

Vicent et al. "Polymer conjugates as therapeutics: future trends, challenges and opportunities", 2008, Expert Opin. Drug Deliv. 5(5):593-614.

Vicent and Duncan, Polymer conjugates: nanosized medicines for treating cancer, TRENDS in Biotechnology 24 (12006):39-47.

* cited by examiner

STEREOISOMER PEPTIDES, LIGAND-TARGETED MULTI-STEREOISOMER PEPTIDE POLYMER CONJUGATES, AND USES THEREOF

CROSS-REFERENCE TO RELATED APPLICATIONS

This application claims the benefit of U.S. Provisional Application No. 61/256,260 filed on Oct. 29, 2009. The above application is hereby incorporated herein by reference.

STATEMENT REGARDING FEDERALLY SPONSORED RESEARCH OR DEVELOPMENT

Not Applicable

TECHNICAL FIELD

This invention relates to synthetic stereoisomer peptides, ligand-targeted multi-stereoisomer peptide polymer conjugate compounds, and uses thereof for the treatment of mammalian diseases.

BACKGROUND

Diseases are the result of abnormal up or down regulation of multiple proteins in the body affecting different physiological pathways. Unregulated angiogenesis, pathological conditions, and pathogen agents cause this abnormal regulation of proteins. The available drugs to treat many of these disease conditions target single proteins and only provide modest and transient clinical effects but do not cure the targeted diseases; hence there is a persisting need to develop multi-targeted therapeutics.

Angiogenesis, the growth of new blood vessels from existing vessels, is an integral component of many physiological and pathological conditions such as wound healing, inflammation, and tumor growth (Folkman, J. and Klagsbrun, M. (1987) Science, 235: 442-447). Under abnormal conditions, angiogenesis can either directly or indirectly cause a particular disease that may include cancer, metastasis, solid tumors, diabetes, inflammation, cardiovascular disease, rheumatoid arthritis, psoriasis, inflammatory diseases, and Alzheimer's and Parkinson's diseases, and related neurological disease conditions, brain disorders, neurodegenerative disorders, neuropsychiatric illnesses, bipolar disorder, and diseases caused by aging. Angiogenesis may also exacerbate an existing pathological condition leading to other diseases, including eye retinopathies such as wet age-related macular degeneration, choroidal neovascularization, diabetic retinopathy, diabetic macular edema, retinal vein occlusion and retinal angiomatus. These angiogenesis-dependent diseases are the result of new blood vessels growing excessively. In these conditions, new blood vessels feed diseased tissues and destroy normal tissues, and in the case of cancer, the new vessels allow tumor cells to grow and establish solid tumors or to escape into the circulation and lodge in other organs leading to tumor metastases.

Growth factors are capable of stimulating cellular growth, proliferation, and cellular differentiation and are involved in most cancers. They are important for regulating a variety of cellular processes and act as signaling molecules between cells (Welsh et al. Amer. J. Surg.194, 2007, S76-S83). Excessive angiogenesis occurs when diseased cells produce abnormal amounts of growth factors or pro-angiogenic factors, overwhelming the effects of natural angiogenesis inhibitors. Pro-angiogenic growth factors may include vascular endothelial growth factor (VEGF-A, B and C), fibroblast growth factor (bFGF), platelet-derived growth factor (PDGF-a/b), epidermal growth factor (EGF), proepithelin (PEPI) or PC cell-derived growth factor (PCDGF) among many others (Marjon P L et al. Molecular Cancer 2004, 3:1-12; Kwabi-Addo B et al. Endocr Relat Cancer. 2004 11(4):709-24).

Cancer is caused by over-expression and up-regulation of growth factors implicated in many physiological pathways and endocrine functions. Abnormal cells divide without control, and migrate and spread to any tissue through the blood and lymph systems (Hanahan D, Weinberg R A. Cell. 2000, 100(1):57-70). The most common cancers include breast, colon, pancreas, prostate, blood, bladder, brain, bone, kidney, lung, liver, skin, ovarian, thyroid, gastrointestinal, head and neck, and neural, among others (Jemal et al. CA Cancer J. Clin. 2008, 58(2):71-96). Progress in cancer research has been slow since there are no drugs to cure cancer; hence, there is a persisting need to develop effective drugs and therapeutic-vaccine compounds that are more stable, more potent, with minimum or no toxicity, and that prolong the life of patients while providing significant improvement in their quality of life.

Pathological conditions of the eye include age-related macular degeneration, choroidal neovascularization, (AMD), proliferative diabetic retinopathy (PDR), diabetic macular edema (DME), among others. These diseases are the result of aberrant proliferation of new blood microvessels or neoangiogenesis (Hubschman et al. Clinical Ophthalmology 2009, 3 167-174). VEGF is a major factor in neovascular eye diseases and is the target by several anti-VEGF based therapies based on monoclonal antibodies. Unfortunately, such therapies induce considerably side effects, thus effective therapies are an unmet medical need.

Inflammation is a process by which the body's white blood cells and chemicals protect the body from infection and foreign substances such as bacteria and viruses. Many pro-angiogenic factors are mediators of inflammation (Campa et al. Mediators of Inflammation, Review Article. 2010, ID 546826, 1-14), and in some diseases, the body's immune system inappropriately triggers an inflammatory response when there are no foreign substances to fight off; in these autoimmune diseases, the body's normally protective immune system causes damage to its own tissues. Multiple sclerosis, type 1 diabetes mellitus, thyroiditis, rheumatoid arthritis and lupus, among others, are autoimmune diseases.

Receptors, found in the extra cellular matrix, are transmembrane proteins that bind ligands. Integrins are receptors for a variety of extra cellular matrix proteins mediating migration of endothelial cells, and regulating their growth, survival, and differentiation, but there are also present on tumor cells of various origins (Cox et al, Nat Rev Drug Discov. 2010, 9(10):804-20). Receptors involved in human diseases include VEGF receptors, G protein receptors, ERBB receptors, platelet derived growth factor receptor (PDGFR), CXR1, CXR2, CCR3, CCR5 receptors, and NOGO receptors, among others. Neurodegenerative diseases and mood disorders are example of diseases caused by the unbalanced neurotransmission of receptors and structural impairment of neuroplasticity. Chronic stress causes decrease of neurotrophin levels inducing depression. Antidepressants like lithium help increase expression of neurotrophins like BDNF and VEGF, thereby blocking, or reversing structural and functional pathologies via neurogenesis. Lithium also induces mood stabilization and neurogenesis due to the inhibition of glycogen synthase kinase-3beta (GSK-3beta), which allows the accumulation of beta-catenin. Increased levels of GSK- 3beta and beta-catenin are associated with various neuropsychiatric and neurodegenerative diseases (Wada A. J Pharmacol Sci 2009, 110, 14-28). Inhibition of GSK-3 beta expression seems therefore beneficial to ameliorate and/or stabilize mood disorders and induce neurogenesis. The unbalanced presence of receptors also causes neurodegeneration. The Nogo receptor binds to the myelin-associated proteins Nogo-A, MAG, and OMgp, causing neurodegeneration. It can inhibit differentiation, migration, and neurite outgrowth of neurons, causing poor recovery of the adult central nervous system (CNS) from damage. Brain-derived neurotrophic factor stimulates the phosphorylation, suppressing Nogo-dependent inhibition of neurite outgrowth from neuroblastoma-derived neural cells; thus, it is important to control Nogo signaling to prevent neuronal damage.

Some proteins in the human body when suppressed exert a positive or beneficial effect. The target of rapamycin, mTOR, when inhibited suppresses the overexpression of HER2 oncoprotein, which is involved in cancer, or inhibits the process of aging by extending the lifespan of organisms (e.g., worms, fruit fly, yeast, and mice); mTOR, is therefore a suitable target to create potential anti-cancer and anti-aging compounds (Liu et al. Nature Reviews Drug Discovery 2009, 8:627-644). Many negative regulators of angiogenesis include thrombospondin-1, brain derived antiangiogenesis inhibitor, angiostatin, tropomyosin, among others. These proteins inhibit endothelial cell proliferation and tumor angiogenesis in vivo.

Diseases caused by pathogen agents include those acquired by blood borne pathogens (e.g., viruses such as HIV) through blood via infected people or animals, blood transfusions, or sexual contact; those caused by infectious agents like prions, which induce their own replication and derive from self; those caused by parasites (e.g., malaria, TB) acquired through bites by host organisms (e.g., insects, rodents), and those caused by pathogens acquired by contaminated food or water, (e.g., bacteria, fungi, yeast).

HIV/AIDS is a worldwide disease of large proportions for which there is no cure (Richman, et al. Science 2009, 323, 1304-1307). Prions contain a protein (PrP) 27-30, which aggregates forming amyloid plaques that accumulate selectively in the central nervous system cells causing neurodegenerative diseases such as Creuzfeldt-Jakob and Alzheimer's diseases, Down's syndrome, fatal familial insomnia, and recently, Parkinson's Disease. Prions are transmitted through contaminated plasma products, meat, and feeds or by person to person (Gu et al. JBC 2002, 277(3):2275-228). There are no drugs to treat prion infection.

Bacterial and parasitic infections are a worldwide health problem. *Staphylococcus aureus* (MRSA) is a highly infectious bacteria and the cause of worldwide nosocomial infections. (Kaufmann et al. Exper. Opin. Biol. Ther. 2008, 8(6): 719-724). Tuberculosis, caused by the pathogenic bacteria *Mycobacterium tuberculosis* (Mtb), is presently the leading cause of death from infectious disease, infecting more than a third of the world's population (Ciulli et al. Chem Bio Chem 2008, 9, 2606-2611). It is acquired from small-infected mammals or by person to person. *Salmonella typhimurium*, other highly infectious and deadly bacteria, spreads by drinking contaminated water (Townes et al. Biochemical and Biophysical Research Communications 2009, 387: 500-503). Malaria, caused by the protozoan *Plasmodium falciparum*, is spread by mosquito bites infecting the red blood cells (Van-Buskirk et al. PNAS, 2009, 106(31):13004-13009). Drugs approved to treat many of these diseases are single target drugs; most are non-specific, and do not cure the aimed disease; hence there is a persisting need to develop novel multi-targeted therapies The diseases described above are the result of the abnormal balance of many proteins involved in different functions and physiological pathways in the body. The available single target drugs, provide a modest and transient clinical effect, but do not cure the aimed disease. Furthermore, clinical trials of drugs targeting many of these diseases have shown numerous times that targeting a single protein or an angiogenesis pathway or a single mechanism, or a disease condition, is unlikely to result in the best possible benefit for the patient. Therefore, it would be advantageous to create compounds comprising multiple different peptides each targeting specifically a particular pathologic protein. This approach may allow simultaneous interference at different levels in the angiogenic cascade or interference of different pathways leading to disease by targeting the functional domains of proteins involved in multiple diseases. For example, targeting simultaneously several proteins involved in abnormal angiogenesis would enable therapeutic applications for eye pathologies, cancer and other diseases. In view of the forgoing, it is appreciated that these multi-targeted compounds would be a significant advancement in the art.

SUMMARY

This invention features novel ligand-targeted multi-stereoisomer peptide-polymer conjugate compounds of the general formula: $(Pol-L_1-sP)_n-Pol-L_2-sP_L$ representing the bonding between polymer Pol with linker $L_1$ and the conjugation of different branches of polymer-linker (Pol-$L_1$) with several different stereoisomer peptides sP represented by integer n [i.e., (Pol-$L_1$-sP)n], n=2 to 100, and the bonding of polymer Pol with linker $L_2$; and the conjugation of this single branch of polymer-linker (Pol-$L_2$) with a single stereoisomer peptide-ligand $sP_L$ [i.e., Pol-$L_2$-$sP_L$] to obtain copolymers, which after radical polymerization, the novel ligand-targeted multi-stereoisomer peptide polymer conjugate compound of the present invention is created. The polymer has a molecular weight no greater than 80 kDa. Most preferably, the polymer has a molecular weight in the range of 20 kDa to 50 kDa.

The invention further refers to the use of ligand-targeted multi-stereoisomer peptide-polymer conjugate compounds as useful therapeutics to treat mammalian diseases. The diseases may include vascular growth, pathological conditions of the eye, cancer, metastasis, inflammation, arthritis, psoriasis, diabetes, and cardiovascular disorders; Alzheimer's, Parkinson's and neurological diseases, brain diseases such as bipolar disease, neurodegenerative diseases, diseases caused by aging, and diseases caused by pathogen agents. The compound may also be a multi-targeted therapeutic-prophylactic vaccine against HIV virus, or a multi-targeted therapeutic against malaria or against bacterial infections caused by MRSA, or *Salmonella*, or the *tuberculosis* bacteria.

The collection of one hundred and fifty two (152) peptides SEQ ID NO 1 through SEQ ID NO 152 ranging 4 to 53 amino acids in length, comprise amino acid sequences with alpha-helix or cyclic structures and with the majority between 7 to 15 amino acids. The peptides mimic short functional domains of natural proteins involved and overexpressed in a variety of human diseases. Peptides SEQ ID NO 1 through SEQ ID NO 117 mimic short domains of proteins involved in abnormal angiogenesis including cancer, growth factors, receptors, and proteins that down regulate angiogenesis. Targets include VEGF, VEGFR, EGFR, PDGFR, heat shock proteins such as HSP90, HSP70, HSP72, and HSC70, kinases and other receptors such as p13K, TAK-1, GSK3, mTOR and NgR; chemokine proteins such as CCL5, CCR3, and CXCR6; the integrins AvB3 and AvB5, and neuroepithelin, proepithelin, XVIII-Collagen, HIV proteins, thrombospondin (TSP-1) and brain derived angiogenesis inhibitor (BDAI). Peptides SEQ ID NO 118 through SEQ ID NO 126 mimic short domains of proteins involved in brain disorders such as those caused by prions (PRNP), Alzheimer's disease and neurodegeneration. Peptides SEQ ID NO 127 through SEQ ID NO 130 mimic short domains of NgR protein involved in diseases of the central nervous system (CNS). Peptides SEQ ID NO 131 through SEQ ID NO 152 mimic short domains of proteins from infectious microorganisms comprising virus, parasite and pathogenic bacteria. Targets include various HIV proteins (e.g., gp120, gp41, Vif, integrase, protease, and reverse transcriptase), PfCDtk1, UIS3, DHFR-TS, Mersacidin, CystatinC, Pep5, peptide-2 Leap-2, Defensin and Acps proteins.

The peptides are not natural peptides but rather are chemically synthesized in their stereoisomer forms containing D- and L-amino acids or only D-amino acids, and may have their carboxy- terminal amidated and/or the amino-terminal acetylated. This provides synthetic peptides that are highly stable, resistant to degradation by enzymes; have extended shelf life; and have longer multi-targeted stereoisomer-peptide polymer conjugate compounds. Their enhanced properties allow administration by several routes, including orally.

In one aspect, this invention relates to the disclosed peptides, which have linear alpha helix or cyclic structures. The alpha helix has a positive net charge with hydrophobic amino acids on one side of the chain and the hydrophilic amino acids on the other side of the chain creating an amphipathic helix. The cyclic peptide is created by two, four or six Cys residues that form single, double or triple intra-molecular disulfide bonds, respectively, via oxidation of SH groups creating constrained cyclic structures.

In another aspect, this invention relates to the conjugation of synthetic linear and/or cyclic stereoisomer peptides to a water-soluble and biocompatible synthetic hydrophilic polymer via a linker to create novel ligand-targeted synthetic multi stereoisomer peptide-polymer conjugate compounds. Polymers used to create compounds to deliver drugs to tissues or cells and cell compartments include polylactide, polyglycolic acid (PGA), polylactic acid (PLA), polyhydroxy acids (PHAs), poly lactic-co-glycolic acid (PLGA), polyethylene Glycol (PEG), and branched PEG, polyvinyl acetate, polyvinyl alcohol, α, β, poly (N-hydroxyetheyl)-DL-aspartamide (PHEA), α, β, poly (N-hydroxypropyl)-DL-aspartamide (PHPA), poly-N-(2-Hydroxypropyl)methacrylamide (HPMA), and HPMA copolymers, polyethylenimine (PEI), polylysine and derivatives thereof. In this invention the compounds comprise different stereoisomer peptides and a peptide-ligand that are independently bound to a functional group of a separate branch of a polymer scaffold via a biodegradable linker creating novel ligand-targeted multi stereoisomer peptide-polymer conjugate compounds. The preferred polymer is N-(2-Hydroxypropyl)methacrylamide) or HPMA, and HPMA co-monomers; the linker may comprise two or more amino acids by addition or substitution preferably selected from Phe, Leu, Lys or Gly, but amino acids such as Ser, Tyr, Gln, GLu, and Asn may also be included.

In one additional aspect, a peptide-ligand is conjugated to the polymer HPMA via a non-degradable linker. The function of the peptide ligand is to guide the delivery of the polymer carrying different stereoisomer peptides to the target site which can be a tissue, cell or a subcellular compartment such as for example the cytosol or nucleus. Preferred peptide-ligands include high affinity peptides, transport peptides, transduction domain peptides, and cell penetrating peptides.

In yet another aspect, this invention relates to the use of the polymer conjugate compounds as specific intracellular carriers of the synthetic stereoisomer peptides into cells via the endocytic pathway. This well characterized cell pathway allows the internalization of the polymer with its cargo. The peptides inside the cells are released from the polymer into the cell cytoplasm, the site of the target proteins, by enzymatic cleavage of the biodegradable linkers.

This invention further refers to peptides that target physiologically and structurally relevant functional domains of proteins. Domains include substrate specific sites, receptor sites, protein-protein interaction sites, docking sites for interacting proteins or receptors, protein specific folding conformations, protein loops, divalent metal ions sites, glycosilation and phosphorylation sites, and cell membrane and transmembrane domains. The desired effect of each peptide candidate, in its stereoisomer modified form, is to prevent, inhibit or block the binding of a protein or a receptor, or a specific substrate or an organic or inorganic molecule to the target protein. The peptide may disrupt protein-protein interactions, protein loop folding, ionic interactions, or the binding of substrates, or the phosphorylation and glycosilation of proteins, or the interaction with the cell membrane. Therefore, the peptides are suppressing, eliminating, preventing, abolishing, blocking or disrupting the physiological activity and/or the conformational structure of the target protein in a mammalian (e.g., animal or human) cell, or a protein important for the function and survival of an infectious microorganism.

The invention further provides novel pharmaceutical compositions comprising formulated linear or cyclic stereoisomer peptides in free form and formulated ligand-targeted multistereoisomer peptide-polymer conjugate compounds. Pharmaceutical compositions of these compounds may be prepared for administration by oral, transmucosal, parenteral, topical, transdermal, and pulmonary routes, and formulated in dosage forms appropriate for each route of administration using pharmaceutically acceptable excipients. Pharmaceutical compositions are for the potential treatment of a variety of mammalian diseases (e.g., animals and humans) described in the anti-disease strategies of this invention.

BRIEF DESCRIPTION OF FIGURES

Features of the invention will be apparent from the following description of the preferred embodiments thereof and from the claims, taken in conjunction with the accompanying drawings, in which:

DETAILED DESCRIPTION

Definitions

Figure 1:
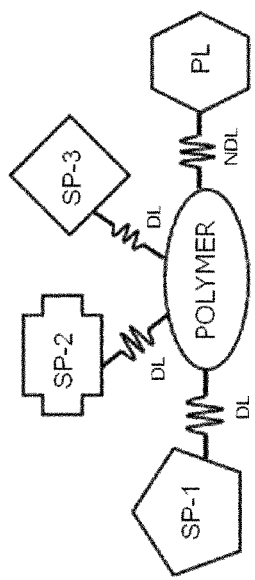
FIG. 1 illustrates the general representation of a novel ligand-targeted multi-stereoisomer peptide-polymer conjugate compound. Where SP-1, SP-2 and SP-3 represent three different stereoisomer peptides, DL represents a degradable linker, NDL represents a non-degradable linker, PL represents a peptide-ligand and Polymer represents HPMA.

The amino acid residues comprising the sequences of the peptides disclosed in the Sequence Listing are abbreviated using a three-letter code. The full names, three letter and single letter abbreviations are as follows: Phenylalanine is Phe or F; Leucine is Leu or L; Isoleucine is Ile or I;

Methionine is Met or M; Valine is Val or V; Serine is Ser or S; Proline is Pro or P; Threonine is Thr or T; Alanine is Ala or A; Tyrosine is Tyr or Y; Histidine is H is or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

As used herein, the term 'peptide' refers to a polymer of amino acid residues, but preferably refers to amino acids that are alpha amino acids joined together through amide bond. Peptides are organic compounds or short polymers created from the linking of two or more α-amino acids in a defined order, and in which the amine of one is reacted with the carboxylic acid of the next to form an amide bond or a peptide bond and refer to peptides up to 100 amino acids in length.

The term 'stereoisomer' or 'enantiomer' refers to peptides comprising amino acids that have two chiral forms that are the mirror image of each other. In this invention, the peptides comprise a mixture of D- and L-amino acids or only D-amino acids and may have two different topologies: In one topology, D-amino acids are the minor image of the naturally occurring (L-amino acid) forms, but do not have the same topology when aligned together; the second topology refers to D-peptides which have similar sequence to that of the natural L-peptides but have the positions of the carboxy- and amino-terminal residues reversed. These D-peptides are also termed retro-all-D-peptides or retro-inversed D-peptides. Most amino acids (except for glycine) are stereoisomers with L- and D-amino acids. Most naturally occurring amino acids are 'L' amino acids. The terms 'D amino acid' and 'L amino acid' are used to refer to absolute configuration of the amino acid, rather than a particular direction of rotation of plane-polarized light. The usage herein is consistent with standard usage by those of skill in the art.

The term 'amphipathic helix' refers to a protein structure that forms an alpha-helix producing a segregation of a polar and nonpolar faces with the positively charged residues residing at the polar-nonpolar interface and the negatively charged residues residing at the center of the polar face.

The term "hydrophilic polymer" refers to a synthetic water-soluble polymer that alters the bio-distribution of a stereoisomer peptide of the invention. Examples of such polymers include, but are not limited to poly(ethylene glycol) (PEG), poly(vinyl alcohol) (PVA), polyvinyl acetate, dextran, hydroxyelthyl starch, gelatin, PVP, PHPMA, .alpha., .beta.-poly[N(2-hydroxyethyl)-DL-aspartamide (PHEA), polysuccinamide (PSI). .alpha., .beta.-poly(N-hydroxypropyl)-DL-aspartamide, among others.

The term "polymer conjugate" refers to a synthetic substance consisting of chemical molecules formed from polymerization and that have conjugated a molecule such as peptide, DNA, RNA, antibody, protein, epitope, or a small chemical, fluorescent, or radioactive molecules via a linker or spacer including but not limited to oligopeptides (di-, tri-, tetra-residues), amide, ester, peptidyl, malonate, aminomalonate, carbamate, and Schiff base.

The term "peptide ligand" refers to any peptide that binds specifically to a specific site on a viral or cellular surface protein and forms a complex. The targeting peptide ligand is conjugated to the polymer using a non-degradable linker. Examples of targeting peptide ligands that provide suitable enhancing of cell targeting include but are not limited to high affinity peptides that interact with growth factors and their receptors; transport peptides that cross the blood barrier in brain, retina, and other tissues; and transduction domain, and cell penetrating peptides which cross the cell membrane.

The term "conjugate compound" refers to a composition comprising a water-soluble polymer with a linker and one or two molecules bound thereto. Preferably, the polymer is HPMA, the linker is a di- tri- or tetra-oligopeptide and the molecule is a stereoisomer peptide, preferably a D-peptide and a peptide-ligand with alpha helix, or beta sheet, or cyclic structure.

The term 'carrier' refers to a water-soluble polymer to which a composition, according to this invention, can be coupled. The carrier increases the molecular size of the compositions providing added selectivity and/or stability. The target molecules are delivered to tissues, cells, and sub-cellular locations. This delivery can be further enhanced by the specificity of the target molecules and a peptide-ligand conjugated to the polymer to create a ligand-targeted polymer conjugate.

The term 'pathogen agent' refers to microorganisms or parasites capable of causing disease, and it is usually restricted to living agents, which include viruses, bacteria, fungi, yeasts, protozoa, and helminthes. Pathogenicity is the ability of an organism to enter a host and cause disease. The degree of pathogenicity, known as virulence, depends on the organism's to cause disease under certain conditions. This ability depends upon the properties of the organism and the ability of the host to raise and immune response.

The term 'formulation agent' refers to both a usually inactive substance used in association with an active substance especially for aiding in the application of the active substance, capable to reach the intended target. Inactive substances include diluents, adjuvant, excipient, or vehicle, which can be sterile liquids, and vegetable or synthetic origin oils. Water or aqueous saline solutions, and aqueous dextrose and glycerol solutions, are preferably employed for injectable solutions.

As used herein, the phrase 'pharmaceutically acceptable' refers to molecular entities and compositions that are 'regarded as safe', i.e., that are physiologically tolerable and do not typically produce an allergic, toxic or adverse reaction when administered to a human. Preferably, as used herein, the term 'pharmaceutically acceptable' means being approved by a regulatory agency of the Federal or a state government or listed in the U.S. Pharmacopeia or other generally recognized pharmacopeia for use in animals, and more particularly in humans. The term "therapeutic agent" refers to a compound that is used in the treatment of mammalian disease, and may be modified, or synthetic. Therapeutic agents generally promote or inhibit any biological process implicated in one or several human disease pathways. Preferred disease targets include, but are not limited to abnormal angiogenesis which includes ocular pathologies, cancer, metastasis, Alzheimer's and Parkinson's disease, neurological disorders, rheumatoid arthritis, diseases of aging to name a few. A therapeutic agent may be, for example, peptide agonists and antagonists, and inhibitors or anti- or pro-apoptotic agents, or modulators.

The term "treating" refers to administering a pharmaceutical composition for therapeutic and/or prophylactic purposes to treat or prevent a mammalian disease. 'Treatment of a disease' refers to treating a patient already suffering from a disease to ameliorate the disease and improve the patient's condition. 'Prevention of a disease' refers to prophylactic treatment of a patient who is not ill. Thus, in the claims and embodiments, treating is the administration of the pharmaceutical composition to an animal or a human either for therapeutic or prophylactic purposes.

Compounds of the Formula Pol (Pol-L$_1$-sP)$_n$-Pol-L$_2$-sP$_L$

The ligand-targeted multi- stereoisomer-peptide-polymer conjugates of this invention have the general formula: (Pol-L$_1$-sP)$_n$-Pol-L$_2$-sP$_L$ represents the bonding between polymer Pol with linker L$_1$ and the conjugation of different branches of polymer-linker Pol-L$_1$ with several different stereoisomer peptides sP represented by integer n [i.e., (Pol-L$_1$-sP)n], n=2-100, and the bonding of polymer Pol with linker L$_2$, and the conjugation of this single branch of polymer-linker (Pol-L$_2$) with a single stereoisomer peptide-ligand sP$_L$[i.e., Pol-L$_2$-sP$_L$] to obtain copolymers, which after radical polymerization, the novel ligand-targeted multi-stereoisomer peptide polymer conjugate compound of the present invention is created. These compounds are useful therapeutics for the anti-disease strategies described in the present invention.

Peptides of the invention

In one aspect, this invention discloses a collection of one hundred and fifty two peptides (152) with sequences labeled SEQ ID NO 1 through SEQ ID NO 152, sizes ranging 4 to 53 amino acids in length, but with the majority between 8 to 15 amino acids, and with alpha-helix or cyclic structures.

In another aspect of this invention, the peptides target specific proteins that cause or exacerbate a disease, or have a positive effect to modulate or prevent a disease; or cause an abnormal physiological condition; or inhibit proteins of pathogenic microorganisms. Although the peptides mimic short domains of natural proteins, all the peptides disclosed in this invention refer to synthetic modified stereoisomer peptides.

Proteins Involved in Human Disease PRNP, and proteins from infectious microorganisms such as Calcium-dependent protein kinase-1 (PfCDPK1), UIS3, and dihydrofolate reductase-thymidylate synthase (DHFR-TS) of the parasite paramecium; Mersacidin from *Bacillus*, Pep5 and Epicidin from *Staphylococcus aureus*; peptide-2 LEAP-2 from *salmonella*, and Acyl Carrier Protein Synthase (Acps) and pantothenate synthetase from *Mycobacterium tuberculosis*. Cystatin C and defensin from human have inhibitory sequences against pathogenic bacteria.

The peptides target functional domains important for the proper folding and function of a particular protein. These functional domains include but are not limited to folding loops, disulfide bridges, alpha-helix and cyclic structures, protein-protein interaction sites, substrate, receptor, and ion binding sites, and phosphorylation and glycosilation sites. Stereoisomer peptides with alpha helix or constrained cyclic structures result in functional, stable, protease resistant linear stereoisomer peptides, and structurally rigid cyclic stereoisomer peptides. These compositions are further conjugated to the preferred polymer to create novel ligand-targted multi-stereoisomer peptide-polymer conjugate compounds, which constitute the subject matter of this invention.

The peptides target the proteins by contacting a particular protein with a particular composition that directs such activity into the cells. The compounds exert their effects by competing, blocking, inhibiting, and/or disrupting a folding structure, an activity, or a functional site of the target protein. Endocytosis of the composition into the cells allow entering the D-peptides inside the cell cytoplasm or nucleus affecting, binding, blocking or competing with other molecules for the sites of the target proteins.

(a) Epidermal Growth Factor Receptor (EGFR)

EGFR, a cysteine rich protein, is the cell membrane receptor for epidermal growth factor. Overexpression of EGFR and dysregulation or increased activity of EGFR signaling pathways promote the growth of malignant tumors like non small cell lung cancer, breast, head and neck, colon, ovarian, pancreatic, bladder cancers and glioblastoma. As a result, EGFR is an important target for therapeutic development. SEQ ID NO 1 through SEQ ID NO 25, derived from EGFR, have terminal Cys residues that form disulfide bonds creating constrained cyclic structures, which are important for protein stabilization. These peptides target the extracellular domain and domain sites involved in receptor binding, glycosilation, phosphorylation, and endocytosis. Peptide SEQ ID NO 25 has alpha-helix structure; it targets the substrate active site of EGFR located in the catalytic domain of the receptor. Peptides from this group are selected to create a novel ligand-targeted multi-stereoisomer peptide-polymer conjugate compound for the potential treatment of small cell lung cancer, colo-rectal carcinoma, glioblastoma, and breast, head, neck, colon, ovarian, pancreatic, and bladder cancers.

(b) Vascular Endothelial Growth Factor A (VEGFA)

VEGF-A is the predominant stimulator of angiogenesis and controls tissue vasculature under normal physiologic conditions through a regulated mechanism of expression. Under pathologic conditions, however, VEGF acts on endothelial cells of existing blood vessels to promote new blood vessel formation, and in the majority of cancers, VEGF is secreted by tumor cells. VEGF initiates the angiogenic process by activating endothelial cells and promoting their migration inducing the angiogenic switch, which is critical to the growth and malignant dissemination (metastases) of solid tumors. Free VEGF binds the receptors VEGFR1 (Flt-1), and VEGFR2 (Flk-1 or KDR), and its expression is driven by oncogene expression and hypoxia, and mediates the effects of other angiogenic molecules playing a central role in the control of tumor angiogenesis. VEGF is, therefore, the key mediator of vasculogenesis, angiogenic remodeling, and angiogenic sprouting.

Given the role of VEGF in cancer and in angiogenesis related diseases, VEGF is the favorite target to develop therapeutics capable of inhibiting its activity under abnormal physiological conditions. Peptides SEQ ID NO 26 through SEQ ID NO 30, mimic functional domains of VEGF including the binding site for heparin and receptor, and the site for dimerization and function of VEGF. SEQ ID NO 26 and SEQ ID NO 27 have alpha-helix structure, and SEQ ID NOs 28, 29 and 30, have terminal Cys residues that form constrained cyclic structures upon oxidation of their SH groups. Peptides from this group are selected to create a novel ligand-targeted multi-stereoisomer peptide-polymer conjugate compound for the potential treatment of non small cell lung cancer, renal cancer, colon cancer, head and neck squamous cell carcinomas, ovarian cancer, cervical cancer, multiple myeloma, leukemia, lymphoma, malignant glioma, vascular and tumor growth, and many pathological conditions of the eye including age related macular degeneration, choroidal neovascularization, diabetic retinopathy, and macular edema.

(c) Heat Shock Proteins (HSP90, HSP70, HSP72, and HSC70)

Heat shock proteins are a group of highly conserved molecular chaperones, which respond to cellular stresses. Heat-shock protein 90 (Hsp90) is an essential chaperon for function and integrity of a wide range of oncogenic client proteins like hypoxia-inducible-factor-1 alpha (HIF-1a), signal transducer and activator of transcription-3 (STAT3), intracellular kinases (Akt, Erk), epidermal growth factor receptor (EGFR), and insulin-like growth factor receptor (IGFR). HSP90 is constitutively expressed at high levels in many cancers, (gastric, liver, Hodgkin lymphoma). Inhibition or blockade of Hsp90 would improve anti-tumoral and anti-angiogenic effects of drugs such as rapamycin and potentially blocking oncogenic signaling molecules. Hsp90 is involved in a variety of regulatory functions including regulation of phosphorylation of SGK-1, which contributes to malignant epithelial cell proliferation. Hsp90 interacts with raptor and regulates mTOR signaling upon T cell activation; regulates Jak-STAT signaling in cells, and modulates the redox status of cytosol in resting and apoptotic cells by reducing Cytochrome C. Peptides SEQ ID NO 31 through SEQ ID NO 35 mimic protein domains important for ATP substrate interaction and binding to Hsp90, and have alpha-helix structure. Peptide SEQ ID NO 34 is a modified short peptide that mimics the C-terminus of the protein.

HSP70 family contains at least eight distinct members, including HSC70, HSP70-8 or HSP73 in the cytoplasm and nucleus; and HSP72 (HSP70, HSP70-1A or HSP70-1B) in the cytoplasm/nucleus/lysosome. Their functions include nascent protein folding; preventing formation of protein aggregates; assisting re-folding of denatured proteins; facilitating their degradation when proteins cannot be repaired; modulating the assembly/disassembly of protein complexes; aiding the translocation of proteins across cellular membranes, and inhibiting cell death. HSP70 levels are abnormally high in a wide variety of tumor cell types and contribute to tumorigenesis and resistance to chemotherapy. HSP70 isoforms, HSP72 and HSC70 are induced in colon and ovarian cancer cell lines exposed to HSP90 inhibitors; and HSC70 modulates HCV infectivity. Important domains of these proteins include ATPase and substrate binding and the interaction with the HSP-organizing protein. Based on the antiapoptotic function of HSP70 isoforms and their essential role in the substrate-loading phase of the HSP90 chaperone cycle, it is important to find inhibitors to silence the activities of both HSP72 and HSC70 and to indirectly inhibit HSP90 chaperone function which may potentially lead to a greater apoptotic effect than that observed with pharmacologic HSP90 inhibitors. The substrate binding sites of heat shock proteins and their interactions with proteins are of functional importance since substrates bind with high affinity and specificity to the C-termini of HSP70, HSP72 and HSC70. Peptides SEQ ID NO 36 through SEQ ID NO 42 mimic domains of HSP72. Peptide SEQ ID NO 37 mimics the C-termini of these proteins. Peptides SEQ ID NO 40 through SEQ ID NO 46 have alpha-helix structure. Peptides from this group are selected to create a novel ligand-targeted multi-stereoisomer peptide-polymer conjugate compound for the potential treatment of diseases caused by a variety of cancers and eye pathologies including age (d) P13K/Atk and p13K/mTOR Phosphoinositide kinases (PIKs) phosphorylate the inositol ring of phosphoinositides, thus acting as signal transducers. Depending on the phosphorylation site on the carbohydrate, PIKs include phosphoinositide 3-kinases (PI3Ks), phosphoinositide 4-kinases (PIP4Ks) and phosphoinositide 5-kinases (PIP5Ks). PI3Ks are further grouped into three classes depending on their subunit structure, their regulation, and their substrate selectivity, and each class contains various isoforms. The PI3K pathway is linked to cancer development and is activated by several growth cofactors and oncogenes. Class I PI3K is a tyrosine kinase that mediates, through its p110a subunit enzymatic activity, the mitogenic signal transduction pathway. P13K is also an effector molecule that interacts with the cytoplasmic domains of growth factor receptors through adaptor subunits containing SH2 domains. PI3K/Atk pathway is activated in multiple myeloma and p13K/mTOR is activated in pancreatic cancer. Malignant gliomas commonly over express the oncogenes EGFR and PDGFR, which contain mutations and deletions of the tumor suppressor genes PTEN and TP53, leading to activation of the PI3K/Akt and Ras/MAPK pathways. Gonadotropin FSH acts via its receptor stimulating the PI3K-AKT pathway. Activation of this pathway occurs in solid tumors, including ovarian epithelial tumors, through mutation of the PI3K subunit genes or inactivation of the tumor suppressor, PTEN. Peptides SEQ ID NO 47 through SEQ ID NO 51 mimic regions of PI3-kinase p110 subunit alpha including the catalytic domain, the ATP binding site, and phosphorylation sites of this protein. Peptides SEQ ID NOs 47, 48, and 50 have alpha-helix structure. Peptides from this group are selected to create a novel ligand-targeted multi-stereoisomer peptide-polymer conjugate compound for the potential treatment of acute gliomas, myeloma, and pancreatic and ovarian cancers.

(e) Transforming-growth-factor-beta-activated Kinase-1 (TAK-1)

TAK-1 is a member of the MAPK kinase and a key regulator in the pro-inflammatory signaling pathway that can be activated by TGF-Beta, IL-1Beta, TNF alpha, and toll-like receptor ligands. In cells, TAK-1 can exist as the catalytic component of two different complexes TAK-1-TAB1-TAB2 or TAK-1-TAB1-TAB3. TAK-1-binding protein-1 is required for TAK-1 activity. TAB2 and TAB3 are adapter proteins containing ubiquitin binding domains which are required for the activation of TAK-1; once activated, it activates the NF-kappa B pathway by interacting with the TNF-alpha receptor-associated factor (TRAF) and phosphorylating the NF-kappa B inducing kinase. TAK-1 phosphorylation also correlates with phosphorylation at Thr-187, and activation of the p38a and JNK pathways via phosphorylation of MAP kinase (MKK) 3/6 and MKK4/7, respectively. Signaling pathways downstream of TNF-alpha are also severely impaired in TAK-1 deficient cells, hence the importance of TAK-1 in the pro-inflammatory signaling pathways. The activation of NF-kappa B is linked to the development and progression of human cancers such as hepatocellular, prostate, and breast carcinoma, and to the conversion of TGF-beta from a suppressor to a promoter of mammary tumorigenesis. The inhibition of important domains of TAK-1 protein provides targets for the development of therapeutics to treat a variety of cancers. Peptides SEQ ID NO 52 through SEQ ID NO 54, with alpha-helix structure, mimic the catalytic domain, the ATP binding site and phosphorylation sites of TAK-1. Peptides from this group are selected to create a novel ligand-targeted multi-stereoisomer peptide-polymer conjugate compound for the potential treatment of pancreatic, liver, prostate, and breast cancers.

(f) Mammalian Target Of Rapamycin (mTOR)

Mammalian target of rapamycin (mTOR) is a large multi-domain serine/threonine protein kinase which plays a central role in the regulation of cell growth, cell proliferation, cell motility, cell survival, protein synthesis, and transcription. This protein is present in cells as mTORC1 and mTORC2, which contain a known binding partner mLST8/GbL, but differ in that the third protein component of mTORC1 is raptor and of mTORC2 is rictor; mTORC2 is involved in regulating the assembly of the actin cytoskeleton in cells and is a key activator of the protein kinase Akt, an essential component of the insulin/PI3K signaling pathway. Akt indirectly activates mTORC1 via phosphorylation-induced inhibition of the complex formed by the tuberous sclerosis proteins TSC1 and TSC2, which acts as a negative regulator of mTORC1 activity; mTORC1 is a downstream effector of mTORC2. Thus, mTOR is an essential target of survival signals in many types of human cancer cells, and its activity is modulated by leucine, rapamycin, and phosphatidic acid; the last two bind to the FRB domain of mTOR.

Many conditions that shift cells from states of nutrient utilization and growth to states of cell maintenance and repair extend lifespan. Inhibition of the nutrient sensor target of rapamycin mTOR increases lifespan. Although rapamycin is used extensively for treating cancers and is extremely selective for mTOR, this drug has very low bioavailability, and can potentially activate pathways that could maintain mTOR active, therefore leading to treatment failure. Thus, the development of selective mTOR kinase inhibitors with higher stability, resistance, and bioavailability is an important unmet medical need. Peptides SEQ ID NO 55 through SEQ ID NO 66 mimic functional domains of mTOR including the ATP binding site and FRB domain, which is the site for binding rapamycin, phospatydic acid and leucine. Peptides SEQ ID NO 59 and SEQ ID NO 61 through SEQ ID NO 66 have alpha-helix structure. Peptides from this group are selected to create a novel ligand-targeted multi-stereoisomer peptide-polymer conjugate compound for the potential treatment of renal, ovarian prostate and liver cancers, and as an anti-aging.

(g) Vascular Endothelial Growth Factor Receptor 2 (VEGFR2)

Cancerous tumors depend on nutrients and oxygen for growth via angiogenesis, wherein new capillaries are formed from existing blood vessels. This is facilitated by VEGF, which is secreted by tumors inducing a mitogenic response through its binding to one of three-tyrosine kinase receptors (VEGFR-1, -2 and -3) on nearby endothelial cells. VEGFR1 is a positive regulator of macrophage migration and regulates VEGFR2 signaling by acting as a decoy receptor. VEGFR2 mediates the major growth effects and permeability associated with VEGF, whereas VEGFR3 is essential for lymphatic vessel formation. Thus, inhibition of this signaling pathway should block angiogenesis and subsequent tumor growth. Endothelial expression of VEGFR2 closely parallels VEGF expression in angiogenic responses. Suppression of the VEGF/VEGFR2 signaling pathway interferes with new blood vessel formation, and thus they are targets for therapeutics. VEGFR-2 also plays a pivotal role in choroidal neovascularization (CNV) development; it is detected on retinal progenitor cells, and is generally considered to promote new vessels. Peptides SEQ ID NO 67 through SEQ ID NO 71 with alpha-helix structures, mimic the catalytic domain, the ATP and substrate binding sites, the activation loop and the amino acids that directly interact or bind inhibitors of VEGFR2. Peptides from this group are selected to create a novel ligand-targeted multi-stereoisomer peptide-polymer conjugate compound for the potential treatment of pathological conditions of the eye like age related macular degeneration, choroidal neovascularization, diabetic retinopathy, and macular edema, malignant brain tumors, thyroid carcinomas, and breast and cervical cancers.

(h) Platelet Derived Growth Factor Receptor-alpha and -beta (PDGFRa and PDGFR-b)

The platelet-derived growth factor (PDGF) family is a potent mitogen for a wide variety of cell types of mesenchymal origin. The PDGF family consists of four members (PDGF-A, PDGF-B, PDGF-C and PDGF-D), which exert their biological effects by binding as homo- or heterodimers to two receptor tyrosine kinases (PDGFRa and PDGFRb). PDGF-AA, PDGF-AB, PDGF-BB and PDGF-CC dimers bind to PDGFRa with high affinity, whereas PDGF-BB and PDGF-DD dimers preferentially bind PDGFR-b. PDGF signaling is critical for embryonic development, whereas in the adult, it is important in wound healing and in the control of interstitial fluid pressure. PDGF is an important factor in regulating angiogenesis and tumor cells. Glioblastomas, fibrosarcomas and osteosarcomas often coexpress PDGF ligands and their cognate receptors leading to autocrine stimulation of tumor cell growth. Both PDGFRa and PDGFRb signaling seems to be involved into regulation of various angiogenic pathways and stromal cell functions. Thus, combined inhibition of PDGFRa and PDGFR-b results in markedly decreased tumor growth in vivo because of impaired recruitment of peri-endothelial cells. PDGFRa is implicated in the growth of gliomas, uterine sarcomas, renal cell carcinoma, and non-small cell lung cancer and PDGFR beta is implicated in chronic myelomonocytic leukemia, renal and non-small cell lung cancer, gastric and esophageal cancers. Peptides SEQ ID NO 72 through SEQ ID NO 78, mimic short sequences of the catalytic domain, and the substrate, ATP and phosphorylation binding sites, important for the overall activity of PDGFRa and PDGFRb. Peptides from this group are selected to create a novel ligand-targeted multi-stereoisomer peptide-polymer conjugate compound for the potential treatment of gliomas, uterine sarcomas, renal cell carcinoma and non-small cell lung cancer; chronic myelomonocytic leukemia, and gastric and esophageal cancers.

(i) PC Cell-derived Growth Factor (PCDGF) or Proepithelin (PEPI)

PC cell-derived growth factor (PCGDF), known as proepithelin (PEPI), granulin-epithelin precursor, GP88, progranulin and acrogranin, plays a critical role in development, cell cycle progression, cell motility, and tumorigenesis. This 90 KDa protein comprise 6-KDa fragments, named granulin A, B, C, D, E, F, and G that correspond to individual domains that have been isolated from a variety of human tissues. The PCDGF gene plays a critical role in tumorigenesis and in several breast cancer cells and its expression correlates with an aggressive phenotype. Overexpression of PCGDF plays a significant role in adipocytic teratoma, glioblastomas, multiple myeloma, and renal cell, gastric and ovarian carcinomas. It also promotes migration, wound healing and invasion of bladder cancer cells, supporting the evidence that PCGDF or proepithelin play as well a critical role in bladder and prostate cancers, and stimulates invasive behavior. Mutations in the PCDGF gene cause fronto temporal dementia leading to neurodegeneration; hence its critical function in regulating survival of neuronal cells. Inhibiting PCDGF impedes the proliferation of breast cancer cells; MDCK renotubular epithelium; ovarian carcinoma; the proliferation of human glioblastomas in culture, all of which are cells from tumor types associated with elevated PCGDF gene expression. PCDGF is therefore, an interesting therapeutic target for the treatment of cancer. Peptides SEQ ID NO 79 through SEQ ID NO 93 are rich in Cys residues forming 2 to 6 disulfide bonds via oxidation of SH groups allowing the formation of constrained cyclic structures. These peptides mimic the sequence domains of three different epithelin modules (epithelin A, D and F) located within the PCGDF protein sequence. Peptides from this group are selected to create a novel ligand-targeted multi-stereoisomer peptide-polymer conjugate compound for the potential treatment of glioblastomas, anaplastic astrocytomas, oligodendrogliomas; uterine sarcomas, renal cell carcinoma, non-small cell lung cancer; chronic myelomonocytic leukemia, and renal, prostate, breast, gastric and esophageal cancers, and laryngeal squamous cell carcinoma.

(j) Neuropilin-2 (NRP-2)

Neuropilin-1 and 2 (NRP-1 and NRP-2) are non-tyrosine kinase transmembrane glycoproteins that share 44% sequence homology. Expression of neuropilins is found in neurons, on inflammatory cells, vascular smooth muscle cells, endothelial cells and tumor cells. Neuropilins are not kinases and can signal via their short intracellular domain directly by recruiting synectin to the cell membrane. NRP expression on tumor cells is correlated with a malignant phenotype in melanoma, prostate, pancreatic cancers, and the formation of tumor-associated lymphatics in lung metastasis. In colorectal cancer, NRP regulates tumor growth. In pancreatic ductal adenocarcinoma (PDAC), NRP-2 shows greater expression than in nonmalignant ductal epithelium. NRP-2 in colorectal carcinoma plays a role in several critical aspects of the malignant; NPR-2 in PDAC is involved in survival signaling, migration, invasion, and anchorage-independent growth in vitro. In vivo, cells deficient in NRP-2 had decreased tumor growth, also associated with a decrease in Jagged-1 expression, a member of the Notch family of ligands and receptors, in the tumor cells. Thus, the reduction of tumor growth may be due to the secondary effect on angiogenesis since there is a decrease in functional vasculature within the tumor. This molecule is therefore a potential therapeutic target. Peptides SEQ ID NO 94 through SEQ ID NO 98 mimic sequences in the a domain of Neuropilin-2 (NRP-2) with ala2 structures important for the binding of Sema3A to neuropilin; and sequences in the b domain with blb2 structures important for the binding of VEGF-165 to neuropilin. Peptides from this group are selected to create a novel ligand-targeted multi-stereoisomer peptide-polymer conjugate compound for the potential treatment of breast, prostate, colorectal, and pancreatic cancers, melanoma, lung metastasis and pancreatic ductal adenocarcinoma.

(k) Integrins Alpha-vβeta3 (αvβ3) and Alpha-vβeta1 (α5β1)

αvβ3- and α5β1-integrins are receptors for a variety of extracellular matrix proteins like vitronectin or fibronectin. Since αvβ3 integrin is expressed in melanoma, glioblastoma, ovarian, and breast cancer, it is an attractive protein target for cancer therapy. High-affinity αvβ3 integrin ligands inhibit angiogenesis, induce endothelial apoptosis, decrease tumor growth, and reduce invasiveness and spread of metastasis. Peptides SEQ ID NO 99 through SEQ ID NO 104 ranging 8 to 14 amino acids in length, mimic sequences of these integrins. These peptides target domains important for the interaction of calcium and the amino acid residues that interact with the tripeptide motive found in a variety of growth factors such as IGF-I, extracellular matrix proteins, and receptor ligands. Peptides SEQ ID NOs 99, 103, and 104 have terminal Cys residues that form disulfide bonds via oxidation of SH groups creating compact cyclic structures. Peptides from this group are selected to create a novel ligand-targeted multi-stereoisomer peptide-polymer conjugate compound for the potential treatment of breast, prostate, colorectal, and pancreatic cancers; tumor growth and metastasis; rheumatoid arthritis, psoriasis, restenosis, and eye diseases including age related macular degeneration, choroidal neovascularization, diabetic retinopathy, and macular edema (l) Chemokines CCL5, CCR3 and CXCR6

Chemokines are small proinflammatory chemoattractant cytokines that bind to G-protein coupled seven-span transmembrane receptors that are major regulators of cellular trafficking. Chemokines induce direct migration of leukocytes along a chemical gradient of ligand(s), and their production is stimulated by proinflammatory cytokines, growth factors and, in general, by pathogenic stimuli arising in inflammatory tissues. In diseased tissues, different tumor cell types trigger a complex chemokine network that influences the quality and quantity of immune-cell infiltration and, consequently, malignant cell proliferation, survival, spread, and angiogenic response. CCL is as a product of activated T cells and an inflammatory chemokine. CCL5 mediates chemotactic activity in T cells, monocytes, dendritic cells, natural killer cells, eosinophils, and basophiles; it is also associated with chronic inflammatory diseases such as rheumatoid arthritis, and inflammatory bowel disease. CCL5 expression levels are associated with melanoma, lung, prostate, pancreatic cancers and breast cancer, and correlate with disease progression; it also modulates cell migration and invasion in several cancer cells. Interaction of CCL5 with its specific receptor CCR on the surface of cancer cells induces cancer invasion. CCL5 and receptor CCR5 increases the migration and expression of matrix metalloproteinases (MMPs), found in human oral cancer cells. Because of the implications of CCL5 with inflammatory diseases and cancer, the protein is a target of interest to develop novel therapeutics. Human eosinophils also respond to a variety of CC chemokines like eotaxin, eotaxin-2, eotaxin-3, which are regulated by T cell expressed and secreted RANTES, monocyte chemoattractant protein (MCP)-2, MCP-3, and MCP-4 through binding to the CC chemokine receptor-3 (CCR3). CCR3, a seven transmembrane domain G coupled receptor, is expressed in eosinophils, Th2 T cells and mast cells. Because of its action on eosinophils and on many cell types that are crucial for induction of an allergic response, eotaxin and the CCR3 receptor are targets of interest for drug intervention. Peptides SEQ ID NO 105 and SEQ ID NO 106 have terminal Cys residues that form disulfide bonds via oxidation of SH groups creating constrained cyclic peptides. The peptides mimic an important functional domain of CCL5 and therefore its interaction with the protein will block the putative receptor-binding site of CCR1, CCR3, CCR4, or CCR5. Peptide with SEQ ID NO 107 with alpha-helix structure mimics a short sequence of the eosinophil eotaxin receptor of CCR3. Peptides from this group are selected to create a novel ligand-targeted multi-stereoisomer peptide-polymer conjugate compound for the potential treatment of diseases caused by inflammatory responses and cancers.

Multiple pairs of chemokines and their receptors play critical roles in cancer progression. CXCL16, a ligand for CXCR6, expresses in a variety of tissues and cells including activated endothelial cells, Hodgkin's disease-derived tumor cells, and tumor-associated macrophages in rectal cancer. CXCL16 also functions as a potent and direct activator of nuclear factor-nB and induces nB-dependent proinflammatory gene transcription through heterotrimeric G proteins, PI3K, PDK-1, Akt, and InB kinase. It also plays a role in the development and progression of atherosclerotic vascular disease. Proangiogenic CXCL16 is a transmembrane molecule transported to the cell surface. The receptor, CXCL16R constitutively expresses in bone marrow and in prostate tissues via CXCR6. The CXCR6/AKT/mTOR pathway plays a central role in the development of prostate cancer (PCa), and alterations of CXCR6 over-expression are associated with invasive growth and angiogenic activities of PCa cells. Thus, blocking the CXCR6/AKT/mTOR signaling pathway is likely to have an antimetastatic effect. Peptides SEQ ID NO 108 through SEQ ID NO 110, with alpha-helix structure, mimic a functional domain located within a loop created by a disulfide bond domain of CXCR6. Peptides from this group are selected to create a novel ligand-targeted multi-stereoisomer peptide-polymer conjugate compound for the potential treatment of prostate cancer.

HIV Tat, Collagen, Thrombospondin (TSP-1) and Anti-Angiogenesis Brain Inhibitor (ABI)

HIV proteins like gp120, gp41, Tat, Vif, protease, integrase, and reverse transciptase contain amino acids that interact with integrins, which in turn mediate binding of virus surface protein to CD4 cells. Tat, a potent transactivator of viral transcription, binds to cellular factors and mediates their phosphorylation, resulting in increased transcription of all virus genes providing a positive feedback cycle. PCDGF (Granulin E region) binds to HIV Tat protein suppressing transactivation by HIV-1 Tat, a key progression factor of Kaposi's sarcoma (KS) due to the presence of amino acid residues that bind αvβ3 integrin promoting its angiogenic activity in vivo. Thus, inhibition of Tat production or prevention of its activity could be a way to inhibit the development and progression of KS in AIDS patients. Tat Cys-rich and basic domains have positive modulatory effect by inhibiting a variety of growth factors, receptors, and cellular activities. HIV Tat inhibit VEGF165 by binding to KDR and neuropilin-1 (NP-1) receptors in endothelial cells. Tat inhibits VEGF induced ERK activation and mitogenesis in endothelial cells; it also inhibits angiogenesis in vitro; inhibit ERK activation induced by basic fibroblast growth factor, and induce cell apoptosis. These properties of HIV-1 Tat protein and its fragments indicate that their major effect in endothelial cells is apoptosis independent of specific inhibition of VEGF receptor activation. Peptides SEQ ID NO 111 through SEQ ID NO 113 mimic domains of HIV tat, protease, vif, reverse transcriptase and gp 120 sequences important for binding to integrins potentially inhibiting cellular processes or pathways related to angiogenesis, and viral infection. The peptides where modified to include terminal Cys residues that form disulfide bonds via oxidation of SH groups creating constrained cyclic structures.

Peptides from this group are selected to create a novel ligand-targeted multi-stereoisomer peptide-polymer conjugate compound for the potential treatment of abnormal angiogenesis induced by the overexpresion of growth factors such as VEGF-165, neuropilin, KDR receptor, integrin and to inhibit HIV.

Type XVIII collagen has positive effects by inhibiting endothelial cell proliferation, migration, and tube formation; suppresses VEGF, and has anti-tumor activity. The protein inhibits phosphorylation of focal adhesion kinase via binding to α5β1 integrin; it is implicated in several signaling pathways, including downregulation of c-myc and RhoA activity, blockage of VEGF signaling, inhibition of the wnt-signaling pathway, and inactivation of metalloproteinases. The association of XVIII collagen with laminin and heparin indicates that different regions of the protein carry out different biological functions, and the disulfide bonds are important for the stability and activity of the protein. Peptide SEQ ID NO 114 is located near to the C-termini of the alpha 1 type XVIII collagen isoform-3 precursor. The peptide terminal Cys residues form a disulfide bond via oxidation of SH groups creating a constrained cyclic peptide. Peptides from this group are selected to create a novel ligand-targeted multi-stereoisomer peptide-polymer conjugate compound for the potential treatment of abnormal angiogenesis, pathological conditions of the eye including age-related macular degeneration, choroidal neovascularization, diabetic retinopathy, and macular edema, and cancer.

Thrombospondin-1 (TSP-1) and brain specific angiogenesis inhibitor (BSAI) are naturally occurring inhibitor of angiogenesis. TSP-1 is a large multifunctional glycoprotein secreted by most epithelial cells and is involved in the organization of the perivascular matrix. TSP-1 blocks all the functions of activated endothelial cells and strongly mitigates tumor growth and metastases, while its absence enhances these effects. Expression of TSP-1 correlates inversely with malignant progression in melanoma, lung, and breast carcinoma. The antiangiogenic effect of TSP-1 has potential as therapeutic for cancer but the many biological activities of TSP-1 make its use very difficult as a cancer therapeutic. TSP-1 has domains that bind to receptors such as two proteoglycan/sulfatide receptors, the integrin αvβ3, CD36 and integrin associated protein (IAP). Given the recognition of these domains by various receptor proteins, they seem to be targets of interest to develop potential therapeutic compounds with antiangiogenic activities. Brain specific angiogenesis inhibitor (BSAI) also contains like TSP-1 similar recognition domains for integrins. Peptides SEQ ID NO 115 through SEQ ID NO 117 mimic domains of TSP-1 and BSAI with terminal Cys residues forming disulfide bonds via oxidation of SH groups creating constrained cyclic structures. Peptides from this group are selected to create a novel ligand-targeted multi-stereoisomer peptide-polymer conjugate compound for the potential treatment of abnormal angiogenesis, cancer, and pathological conditions of the eye including age related macular degeneration, choroidal neovascularization, diabetic retinopathy, and macular edema.

(n) Glycogen Synthase Kinase-3 Beta Isoform-1 (GSK3 Beta)

Lithium is used to treat mood and manic-depressive illness, as well as acute brain injuries like ischemia, and chronic neurodegeneration, which are attributed to decreased expression of neurotrophins like BDNF and VEGF. Its beneficial effects include mood stabilization, behavioral amelioration, and neurogenesis due to inhibition of glycogen synthase kinase-3β (GSK-3β), a serine/threonine protein kinase, which promotes β-catenin-dependent transcriptional events. Antidepressants up-regulate expression of IGF-I which in turn up-regulates brain-derived neurotrophic factor (BDNF), its receptor TrkB, and GSK-3, which controls cell membrane signal-to-gene transcription/protein translation, cytoskeletal organization, neuronal polarity, and cell survival/apoptosis. Consistent with these pleiotropic roles, GSK-3β activity is regulated via phosphorylation, subcellular translocation, and interaction with other proteins and is enriched in the nervous system. GSK-3β is constitutively active in nonstimulated cells under the basal quiescent state, it continuously phosphorylates signaling molecules like glycogen synthase, transcription factors like β-catenin, translational initiation factor eIF2B, and structural proteins like tau, thereby keeping these GSK-3 substrates in an inactive state or promoting their degradation. Stimulation of a variety of receptor tyrosine kinases phosphorylate GSK-3α/3β; this phosphorylation event inhibits the catalytic activity of GSK-3α/3β, thereby turning on signaling pathways otherwise constitutively suppressed by GSK-3α/3β in nonstimulated quiescent cells. GSK-3β is of interest because its dysregulated hyperactivity is associated with insulin resistance, diabetes mellitus, tumorigenesis, inflammation, and neuropsychiatric and neurodegenerative diseases. β-Catenin is phosphorylated by GSK-3β, leading to its proteasomal degradation; lithium prevents GSK-3β-catalyzed phosphorylation of β-catenin, enabling β-catenin to accumulate and translocate to the nucleus, where it facilitates gene transcription. It is clear, that GSK-3β/β-catenin pathway is the convergent therapeutic target of lithium and various classical neuropsychiatric drugs, ameliorating behavior, mood, anxiety, cognition, and neurogenesis; hence GSK-3 β interest as target to develop therapeutics to treat neurodegenerative diseases of the brain. Drugs for Alzheimer's disease have not shown significant likelihood of success; hence the opportunity to develop innovative drugs for this unmet medical need. Peptides SEQ ID NO 118 through SEQ ID NO 121 mimic functional domains of GSK-3β including phosphorylation, substrate binding pocket, and ATP binding sites, which are essential for GSK-3 β function. Peptides from this group are selected to create a novel ligand-targeted multi-stereoisomer peptide-polymer conjugate compound for the potential treatment of neurodegeneration, Alzheimer's disease, and bipolar disease.

(o) Prion and Alpha-synuclein

Infectious agents called prions are the cause fatal neurodegenerative disorders of mammals characterized by a pathological process mediated by an abnormal form of a physiological protein called prion. Under certain circumstances, prion protein in nervous tissue assumes a conformation rendering the protein resistant to normal physiological turnover processes. The abnormal prion accumulates in nervous tissue resulting in the typical spongiform changes. A prion is therefore a fatal infectious agent composed primarily of protein that affects the structure of the brain or other neural tissue. Prion has alpha-helical conformation and resides on the surface of cell membranes; when it misfolds, acquires high beta-sheet content and assembles into rods that coalesce aggregating extracellularly within the central nervous system to form amyloid plaques, which disrupt the normal tissue structure. Diseases caused by prions in humans include Creutzfeldt-Jakob disease and Alzheimer's disease among others. PRNP, the gene for the normal protein, show mutations in all inherited cases of prion disease. The mutations change the normal protein into the abnormal form. Parkinson's disease (PD) is an age-related neurodegenerative disease characterized by a loss of dopamine neurons in the substantia nigra pars compacta coupled with proteinaceous inclusions in nerve cells and terminals, known as Lewy bodies and Lewy neurites, respectively. PD pathology affect nondopamine neurons in the upper and lower brainstem, olfactory system, cerebral hemisphere, spinal cord, and autonomic nervous system. The cause of cell death in PD is unknown, but proteolytic stress with the accumulation of misfolded proteins is implicated. Lewy bodies are the hallmark of PD and are composed of aggregated proteins that include alpha-synuclein (NACP). Similar to prion, alpha-synuclein acquires a largely alpha-helical conformation when it binds to cell membranes. When alpha-synuclein misfolds, it acquires high beta-sheet content and polymerizes into fibrils that are associated with the formation of Lewy bodies. Overexpression of alpha-synuclein alone can induce PD syndrome in animals and humans. Alpha-synuclein behaves like a prion, and thus PD seems to be a prion disorder. Since both prion and alpha-synuclein lead to a prion disorder, both proteins are target molecules of interest. Peptides SEQ ID NO 122 through SEQ ID NO 126 mimic domains of PrP and Alpha-synuclein. Peptides SEQ ID NO 122 and SEQ ID NO 124 are designed with motives similar to the kringle domain repeats of plasminogen, to bind prion protein. Peptide SEQ ID NO 125 is a modified linear octapeptide that mimics a domain near to the C-termini of a-synuclein, and may block phosphorylation. Peptide SEQ ID NO 126 mimics a sequence located at the N-terminal near to KTK repeats of NACP protein. Peptides from this group are selected to create a novel ligand-targeted multi-stereoisomer peptide-polymer conjugate compound for the potential treatment of CJD, PD, Alzheimer's, and neurodegenerative diseases.

(p) NOGO Receptor (NgR)

Neurons in the CNS normally do not regenerate after damage due to inhibitors of axon regeneration in CNS myelin, since different proteins expressed on mature oligodendrocytes cause axonal growth cones to collapse and thus arrest further growth. In addition, neurotrophic factors and growth-associated proteins, which are expressed in injured peripheral nerves, are often absent in the adult CNS. Furthermore, proteoglycan-rich glial scar at the lesion site forms a physical and molecular barrier to re-growth. Thus, a major goal in the search for therapies for spinal cord injuries (SCIs) is to develop drugs that promote both the regeneration of damaged axons and the restoration of synaptic contacts with their appropriate targets. The axon regeneration inhibitor Nogo is a myelin-associated neurite outgrowth inhibitor. Nogo, myelin associated glycoprotein, and oligodendrocyte myelin glycoprotein, are interesting targets to develop spinal cord injury therapeutics. Activation of NgR results in a decrease in cellular cAMP. Peptides SEQ ID NO 127 through SEQ ID NO 130 mimic a structural domain where two prominent clusters, the acidic and hydrophobic cavities are located. These regions are important for protein-protein interactions and with extensive well-packed receptor-ligand binding interfaces with polar residues linked in complementary electrostatic interactions, and thus this region offers unique structures for the binding of substrates and potential inhibitors. These peptides have terminal Cys residues that form disulfide bonds via oxidation of SH groups creating compacted cyclic structures. Peptides from this group are selected to create a novel ligand-targeted multi-stereoisomer peptide-polymer conjugate compound for the potential treatment of spinal cord injury (SCI) and central nervous system (CNS) injury where axon regeneration and/or neurite outgrowth is required for functional recovery.

(q) HIV-1 gp120, gp41, p24, Protease, Reverse Transcriptase, Integrase, and Vif

HIV is an infectious pathogen and a global health problem of unprecedented dimensions. The identification of effective inhibitors or a vaccine is an unmet medical need. The envelope glycoprotein gp120, integrase, reverse transcriptase, vif and protease have sequences of interest that can be used to develop an inhibitor or a therapeutic-prophylactic vaccine. Peptides SEQ ID NO 131 to SEQ ID NO 134, from HIV Subtype B strain HXB2 mimic domains of the proteins gp120, gp41, p24, protease, integrase, reverse transcriptase, and Vif. Peptides from this group are selected to create a novel ligand-targeted multi-stereoisomer peptide-polymer conjugate compound for the potential treatment and prevention of HIV/AIDS.

(r) Calcium-Dependent Protein Kinase-1 (PfCDPK1), UIS3 and Dihydrofolate Reductase-Thymidylate Synthase (DHFR-TS)

Malaria, caused by *Plasmodium falciparum* infections, is a global health problem affecting 500 million people worldwide annually resulting in about one million deaths per year. The need to develop an effective anti-malaria therapeutic vaccine is an unmet medical need. Peptides SEQ ID NO 135 through SEQ ID NO 137, mimic short domains of calcium-dependent protein kinase-1 (PfCDPK1), a protein essential for parasite survival. The domains include ATP binding site, substrate-binding pocket and the calcium-binding site. UIS3 protein plays a central role in fatty acid/lipid import during the rapid parasite growth in hepatocytes. This protein has a compact alpha-helical structure that binds to one molecule of the lipid phosphatidylethanolamine. The parasite relies on host fatty acids for synthesis of its membranes. Peptide SEQ ID NO 137 with alpha-helix structure mimics a domain of UIS3 protein.

Dihydrofolate reductase-thymidylate synthase (DHFR-TS) occurs as a bifunctional protein in malaria. The two proteins fuse together to form a single polypeptide. DHFR-TS is an essential enzyme in folate biosynthesis and therefore a drug target of interest to identify peptide sequences that could be used to develop a therapeutic to prevent the conversion of dihydrofolate to tetrahydrofolate by DHFR. Peptides SEQ ID NO 138 through SEQ ID NO 141 mimic the NADP and folate binding sites of DHFR, respectively. The peptide SEQ ID NO 140 has terminal Cys residues that form a constrained cycle structure via oxidation of the SH groups. Peptide SEQ ID NO 141 is a linear proline/lysine rich peptide.

Peptides from this group are selected to create a novel ligand-targeted multi-stereoisomer peptide-polymer conjugate compound for the potential treatment of the malaria parasite.

(s) Mersacidin, Cystatin C, and Pep5

*Staphylococcus aureus*, a gram-positive bacteria enclosed in a thick cell wall and associated with significant morbidity and mortality, is a pathogen responsible for diseases including pneumonia, endocarditis, and bacteremia. Methicillin-resistant *Staphylococcus aureus* (MRSA) is the most common cause of nosocomial infections. It is of medical relevance since methicillin resistance has originated in strains not associated with nosocomial environments and/or antibiotic exposure. *S. aureus* is limited by a single membrane that comprises negatively charged phospholipids. The bacteria is surrounded by a thick cell wall of peptidoglycan. The membrane provides a barrier of selective permeability and the cell wall protects the bacteria from environmental factors. Both structures are essential for cell survival and hence the opportunity to identify therapeutics that target the bacteria cell wall and membrane. Several proteins of interest include Mersacidin from *Bacillus* sp, Cystatin C from human, and Pep5 from *Staphylococcus epidermidis*. Mersacidin inhibits the transglycosylation of peptidoglycan biosynthesis of the cell wall and has a propeptide modified to the mature lantibiotic during biosynthesis. The sequence contains Abu (2-aminobutyric) residues that are replaced with Cys residues to maintain the ring structure, which confers chemical stability and proteolysis resistance of the peptide. Peptide SEQ ID NO 142 is therefore a cyclic peptide with four site-specific disulfide bonds formed via oxidation of eight Cys residues. This peptide is designed to target the cell wall of gram-positive bacteria. A second example is human Cystatin C, a cysteine protease inhibitor of bacteria containing this protease. Peptide SEQ ID NO 143 mimics a domain where the antibacterial activity is present. A third example is a peptide identified from the antibiotic peptide Pep5 derived from *Staphylococcus epidermidis*. The bactericidal activity of Pep5 is towards gram+ bacteria such as MRSA, and consists of depolarization of energized bacterial cytoplasmic membranes, initiated by the formation of aqueous transmembrane pores. This peptide in its natural form contains lanthionine-amino acids that form thioether bonds with Cys residues to form a cyclic structure. The lanthionine amino acids are replaced by Cys residues, which form disulfide bonds via oxidation of SH groups, which maintain the ring structure of the peptide further enhancing its stability and resistance to degradation. Peptide SEQ ID NO 144 forms three site-specific disulfide bonds via oxidation of Cys residues. A fourth example is Epicidin of *Staphylococcus epidermidis*. This peptide contains also lantibiotic amino acids that form a ring structure via thioether bonds with Cys residues. The lantibiotic amino acids where replaced with Cys residues to maintain the cyclic structure via disulfide bonds. Peptide SEQ ID NO 145 forms three site-specific disulfide bonds via oxidation of Cys residues. Peptides from this group are selected to create a novel ligand-targeted multi-stereoisomer peptide-polymer conjugate compound for the potential treatment of MRSA, the bacteria responsible for nosocomial infections.

(t) Peptide-2 LEAP-2 and Defensin

*Salmonella typhimurium* is a pathogenic Gram-negative bacteria predominately found in the intestinal lumen. Its toxicity is due to an outer membrane consisting largely of lipopolysaccharides (LPS) which protect the bacteria from the environment. The LPS is a polysaccharide core, and lipid A, which is made up of two phosphorylated glucosamines, which are attached to fatty acids. These phosphate groups determine bacterial toxicity, and the antigen being on the outermost part of the LPS complex is responsible for the host immune response. *S. typhimurium* undergo conformational changes by acetylation of its antigen, making it difficult for antibodies to bind. *S. typhimurium* infects by coming in direct contact with nonphagocytic cells. This contact induces the formation of appendages on the bacterial cell surface causing host cytoskeleton to rearrange and allowing the bacteria to enter the cell causing gastroenteritis that lead to diarrhea. Peptides SEQ ID NO 146 through SEQ ID NO 148 mimic short domains of peptide-2 LEAP-2 and defensins with potential inhibitory effect against Gram + and –bacteria, yeast, virus and fungi. They may be useful membrane and killing the pathogens. Peptides from this group are selected to create a novel ligand-targeted multi-stereoisomer peptide-polymer conjugate compound for the potential treatment of *Salmonella*.

(u) Acyl Carrier Protein Synthase (Acps)

Tuberculosis (TB) is caused by *Mycobacterium tuberculosis* (Mtb) claiming the lives of millions of people each year, and with about one third of the world's population already infected with Mtb. Fatty acid synthesis and their elongation to mycolic acids, the hallmark of mycobacterial cell wall, is an essential process for bacteria survival. The acyl carrier protein synthase (AcpS) is a trimeric protein comprised of three asymmetric monomers. This protein activates two distinct acyl carrier proteins (ACP-1 domain and the mycobacterial AC-II protein) that are present in fatty acid synthase systems FAS-I and FAS-II, respectively. AcsP binds to ACP-1 and ACPM through different amino acid residues and interactions. The structural characteristics of Mtb AscP protein and the mode of interaction with ACPM and FAS-I are essential for Mtb viability; thus, the protein is a target for the development of drugs. Peptide SEQ ID NO 149 mimics a functional domain important for CoA binding, salt bridge formation, and the binding interaction sites of ACP-II and ACPM proteins. Pantothenate synthetase, the product of the panC gene, is also a protein essential for Mtb. Pantothenate (vitamin B5) is the essential precursor to coenzyme A and acyl carrier proteins. The de novo biosynthetic pathway to pantothenate is present in many bacteria, fungi, and plants and comprises four enzymes, encoded by panB, panE, panD, and panC. This protein and the pantothenate pathway are therefore attractive target for inhibitors that could provide lead compounds for novel anti-TB drugs. Since no panF homologues have been identified in Mtb, TB cannot acquire pantothenate from the environment. The absence of these enzymes in mammals further suggests that inhibitors could be selective with a reduced risk of side effects. Peptides SEQ ID NO 150 through SEQ ID 152 mimic the catalytic site of substrates and products important for pantothenate synthetase enzyme catalytic mechanism. Peptides from this group are selected to create a novel ligand-targeted multi-stereoisomer peptide-polymer conjugate compound for the potential treatment of Mtb infections, the causal agent of *tuberculosis*.

Peptides SEQ ID NO 1 thru SEQ ID NO 152 from natural proteins sequences of human and pathogen agents, illustrate the advantages of the present invention and are not intended in any way otherwise to limit the scope of the disclosure.

A particular aspect of this invention is that all the peptides are synthesized in their stereoisomer forms comprising L- and D-amino acids or only D-amino acids giving rise to alternative stereo-chemistries, which will be readily appreciated by those skilled in the art. Peptides comprising D-amino acids are the preferred form of the peptides of this invention.

In another aspect, this invention provides peptide compounds with modified ends by acetylating the N-terminal group and amidating the C-terminal group using standard chemistries. These additional modifications mimic a peptide bond at the end of the peptide, further increasing their stability to proteases and further yielding enhanced pharmaceutical properties. The N-terminal group, however, is not protected when the peptide is conjugated to a linker.

Both chiral changes and end terminal protection creates peptide compounds that are resistant to proteolysis and can readily be conveniently administered by several routes including the oral or mucosa routes. A review of the available literature shows that multiple alternating L- and D-amino acids or synthesizing peptides containing only D-amino acids helps to enhance their stability and resistance to degradation by enzymes. Peptide chirality (i.e., D- and L amino acids or only D amino acids) is not necessarily required for biological activity or for peptide-peptide interactions within the membrane environment, and therefore they should exert their biological activity like their natural counterparts (L-forms) do. Furthermore, peptides with D-amino acids are not degraded by proteases providing potential for oral bioavailability, since they have extended persistence in circulation, long shelf life, and can be used in harsh mucosal environments as a topical prophylactic microbicide, and are resistant to hydrolysis. Natural and synthetic peptides with L-amino acids lack all these properties in vivo; in fact, peptidases break peptide bond in L-peptides by inserting a water molecule across the bond.

Generally, L-peptides are degraded by peptidases in the body in a manner of a few minutes or less. Some peptidases are specific for certain types of L-peptides, making their degradation even more rapid. Thus, if a peptide is used as a therapeutic agent, its activity is generally reduced as the L-peptide quickly degrades in the body due to the action of peptidases; in this invention, instead of synthesizing the peptides in their naturally occurring forms (L-peptides), the chirality of the amino acid sequence is changed by synthesizing the peptides with mixtures of D- and L-amino acids or entirely with D-amino acids, the preferred form, to create stereoisomer peptide compounds with enhanced stability, solubility, and resistance to degradation by enzymes. These D-peptides comprise both inversed D-peptides and retro-inversed D-peptides. These enhanced physicochemical properties make target specific stereoisomer peptides suitable to develop novel stable drugs for therapeutic use.

Peptide Modifications: Protecting Carboxy- and Amino-terminal Groups

The peptides disclosed here mimic natural sequences of protein domains, but they are synthesized in their stereoisomer forms with modified ends using standard chemistries known in the art. These modifications remove the electrical charges that interact with other peptides and/or proteins by creation of a peptide bond at the ends of the peptide. Peptide compounds can also be modified to obtain a derivative thereof such as alpha-chloroacetic acid, alpha-bromoacetic acid, or alpha-iodoacetic acid, or by phosphorylation, and other methods. Without being bound by a particular method or theory, blockage, particularly of the amino and/or carboxyl terminal of the subject peptide compounds of this invention, greatly enhances pharmaceutical properties and improves oral delivery by significantly increasing serum half-life, and stability to peptidases and other enzymes. A wide number of protecting groups known in the art are described in Greene et al, 1991, Protective Groups in Organic Synthesis, 2nd ed., John Wiley & Sons, Inc. Somerset, N.J.

Stereoisomer Peptides

The peptides disclosed in the sequence listing refer to synthetic chiral or stereoisomer peptides containing both L- and D-amino acids and all D-amino acids. While both L- and D-amino acids can be combined in a peptide chain, the stereoisomer peptide preferred here contain mainly D-amino acids giving rise to alternative stereochemistries, which will be readily appreciated by those skilled in the art. These D-peptides comprise both topological forms represented by inversed D-peptides and retro-inversed D-peptides. Inversed D-peptides are the mirror image of L-peptides and therefore they do not overlap. Retro-inversed D-peptides retain the original spatial orientation of all side chains as in the L-peptides and they overlap.

These modifications provide synthetic peptide compounds that are highly stable, are resistant to degradation by proteases present in human fluids, and have extended persistence in circulation and have longer shelf life. These properties further provide adequate pharmaceutical properties, including reduced to none immunogenicity; can readily be administered by the oral or mucosal routes, and have enhanced biological activity given the high degree of stability. Furthermore, peptide chirality is not necessarily required for biological activity or for peptide-peptide interactions within the membrane environment. These characteristics make stereoisomer peptides with L- and D-amino acids or only with D-amino acids useful to develop stable molecules for therapeutic purposes. Examples of enantiomers of natural proteins and polypeptides derived from a phage-based library are disclosed in U.S. Pat. No. 5,780,221; the polypeptides and peptides of the library are used to identify the enantiomers. In contrast, we use in the present invention natural macromolecules, i.e., proteins, to identify L-peptides from functional domains of target proteins, and then the peptides are synthesized in the stereoisomer forms comprising L- and D-amino acids, but preferably all D-amino acids to create D-peptides including their analogs inversed D-peptides and retro-inversed D-peptides.

Peptide-ligands

Peptide-ligands are usually small peptides that either bind to epitopes and induce an immune response or can bind with high affinity to receptors, hormones, cytokines, enzyme substrates, viruses, proteins and a variety of other macromolecules. Peptides-ligands and their analogs, may antagonize or modulate the physiological action of the natural ligands of the macromolecule (i.e., proteins) directly (competitive) or indirectly (allosteric), and as such they are useful to guide the delivery of drugs to target sites. These peptides constitute transduction domains (e.g., Tat TD), cell penetrating peptides (e.g., penetratin), permeation peptides that cross the blood brain or retina barrier, and transport peptides (e.g., transportan). The antagonistic effect of these peptides may include inhibitory activities. Suitable inhibitory peptides may include tyrosine kinase antagonists; angiogenesis inhibitors; apoptosis regulators; basic fibroblast growth factor inhibitor; cartilage derived inhibitor; kinase inhibitors, insulin-like growth factor-1 receptor inhibitor; interferon agonists; interferons; interleukins; lytic peptides; matrix metalloproteinase inhibitors; signal transduction inhibitors; signal transduction modulators; somatomedin binding protein; splenopentin; spongistatin; squalamine; tyrosine kinase inhibitors; urokinase receptor antagonists. Other peptides may be derived from GnRH, insulinlike growth factor, heparin, platelet factor-4, beta-amyloid peptides, delta-opioid antagonists, chemotactic peptides, epidermal growth factor, plasmin inhibitor, antimicrobial peptides, thrombospondin receptor, pituitary adenylyl cyclase type I and those derived from phage display libraries.

Peptide Synthesis

The peptides of the invention may be prepared by classical chemical synthesis methods well known in the art. Techniques for solid phase synthesis are very advanced and well known to those of skill in the art and are described, for example, by Stewart JM and Young JD, 1984, Solid phase peptide synthesis (2nd ed.). Rockford, Pierce Chemical Company; Atherton E and Sheppard R C, 1989, Solid Phase peptide synthesis: a practical approach. Oxford, England: IRL Press; and Henklein et al, 2008, J. Peptide Science 14 (8): P10401-104). Solid phase synthesis is typically commenced from the C-terminal end of the peptide using an alpha-amino protected resin. After initial coupling, the alpha-amino protecting group is removed using trifluoroacetic acid (TFA) or hydrochloric acid (HCl) solutions in organic solvents at room temperature. Thereafter, alpha-amino protected amino acids are successively coupled to a growing support-bound peptide chain. The alpha-amino protecting groups, including protection of side chains, are those known to be useful in stepwise synthesis of peptides, and include a variety of protecting groups well known in the art. After the desired amino acid sequence has been completed, the desired peptide is decoupled from the resin support by treatment with a reagent, such as trifluoroacetic acid (TFA) or hydrogen fluoride (HF), which not only cleaves the peptide from the resin, but also cleaves all remaining side chain protecting groups. The chemical synthesis of peptides with D-amino acids is similar to the synthesis of peptides with L-amino acids. The purification process is carried out using standard HPLC, or by dialysis. D-amino acids are incorporated at one or more positions in the peptide simply by using a D-form derivatized amino acid residue in the chemical synthesis. D-amino acid residues for solid phase peptide synthesis are commercially available from a number of suppliers. The D-amino acids are incorporated at any position in the peptide as to obtain peptides with L- and D-amino acids or the peptide can be synthesized entirely with D-amino acids.

Stereoisomer Peptides with Linear Structure

In an embodiment of this invention, some of the amino acid sequences selected have linear structure forming a combination of H-helix, E-strand and C-coil structure, which negative or positive charge, and with only a few hydrophobic residues. In this case, the short sequence may specifically target a substrate site or the binding pocket of a substrate, and the Cys residues, when present may not necessarily form disulfide bonds.

Stereoisomer Peptides with Alpha-helix and Cyclic Structures

In another embodiment of this invention, the peptides contain two important structural characteristics, alpha-helix and cyclic structures, making them more effective as potential therapeutic compounds. The first characteristic includes peptides with amino acid sequences that form an alpha-helix, have a net positive charge, and a percentage of the hydrophobic residues located on one side of the chain, with both hydrophobic and hydrophilic amino acids forming an amphipathic-helix. Examples of synthetic peptides with alpha-helix configuration and with a modulating activity are found in many human and bacterial proteins like cathelicidin, from human, and Gramicidin A, from bacteria. These peptides with amino acids arranged in the alpha-helix configuration have the property to bind and permeate the negatively charged membranes and therefore are useful as therapeutics, since they readily penetrate cell membranes. Peptides with similar configuration but containing stereoisomer amino acids are designed from the protein of interest to obtain effective therapeutics.

The second structural characteristic of the peptides of this invention refers to peptides with amino acid sequences that have 2, 4, or 6 Cys residues that form single, double or triple intra-molecular disulfide bonds via oxidation of their SH groups, respectively, to obtain cyclic structures with constrained conformation. The rigidity of the cyclic peptide depends upon the number of disulfide bonds, which is determined by the number of Cys residues present in the peptide chain. This property makes the cyclic peptides highly stable and therefore potentially affecting the function, folding, or interaction of the target protein. Cyclization of peptides not only forms constrained structures but also greatly increases protease resistance. In this invention, the chiral peptides with cyclic structure are designed with molecular rigidity to enhance their physicochemical and pharmaceutical properties.

Cyclization of Stereoisomer Peptides by Disulfide Bond Formation

Disulfide bridges are an important subject matter of this invention. Several peptides disclosed in this invention may contain one, two, or three intramolecular disulfide bonds that are formed by oxidation of the Cys residues by pairing the desired Cys residues through the SH groups present in the sequence of a particular synthetic stereoisomer peptide containing L- and D-amino acids, or only D-amino acids. In one embodiment of this invention, the control of Cys bond formation is exercised by choosing an oxidizing agent of the type and concentration effective to optimize formation of the desired disulfide bond. In general oxidation is carried out chemically using a catalyst. For example, oxidation of the Cys residues of a stereoisomer peptide to form one, two, or three intramolecular disulfide bonds is achieved using the oxidizing agent DMSO or iodine ($I_2$). For example, cyclization is achieved by dissolving the SH-group containing peptide in a phosphate or bicarbonate aqueous buffer at pH 7-9. The concentration of the peptide is approximately 1 mg/ml or less. Nonaqueous solvent such as DMF, DMSO or methanol could be used alone or with water along with an appropriate proton scavenger such as triethylamine or diisopropylethylamine. The cyclized peptide is purified using high performance liquid chromatography (HPLC) and often times the cyclized peptide will elute earlier than the uncyclized precursor. This is due to the diminished available hydrophobic surface area in the cyclized peptide, which minimizes its interaction with the reversed phase matrix. The cyclization can take from 15 minutes to 24 hours depending on the specific conditions used; typically room temperature, solvent, peptide composition and solubility of the peptide. The reaction can be monitored by HPLC or with Ellman's reagent, which allows monitoring the amount of free SH— group being consumed. In other embodiments, and preferably, the formation of Cys bonds is controlled by the selective use of thiol-protecting groups during peptide synthesis. For example, where two intramolecular disulfide bonds is desired, the peptide chain is synthesized with the four Cys residues of the core sequence protected with a thiol protecting group. Thereafter, the thiol protecting groups are removed from the Cys residues where the disulfide bond is desired effecting bisulfide cyclization of the monomer chain. In addition to the foregoing cyclization, strategies described and preferred here, other non-disulfide peptide cyclization strategies can be employed, especially when cyclization is carried out with other amino acid residues. Such alternative cyclization strategies include, for example, amide-cyclization strategies as well as those involving the formation of thio-ether bonds. Thus, the compounds of the present invention can exist in a cyclized form with either an intramolecular amide bond or an intramolecular thio-ether bond. For example, a stereoisomer peptide may be synthesized wherein one Cys of the core sequence is replaced with lysine and the second Cys is replaced with glutamic acid.

Thereafter a cyclic monomer may be formed through an amide bond between the side chains of these two residues. Alternatively, a peptide may be synthesized wherein one Cys of the core sequence is replaced with lysine (or serine). A cyclic monomer may then be formed through a thio-ether linkage between the side chains of the lysine (or serine) residue and the second Cys residue of the core sequence. As such, in addition to disulfide cyclization strategies, amide-cyclization strategies and thio-ether cyclization strategies can both be readily used to cyclize the compounds of the present invention. Alternatively, the amino-terminus of the stereoisomer peptide can be capped with an alpha-substituted acetic acid, wherein the α-substituent is a leaving group, such as an alpha-haloacetic acid, for example, alpha-chloroacetic acid, alpha-bromoacetic acid, or alpha-iodoacetic acid.

Cyclization of stereoisomer peptides containing 2, 4 or 6 Cys residues may also be carried out through disulfide bonds using either ferricyanide assisted cyclization or glutathione assisted oxidation reactions. This can be carried out using highly purified stereoisomer peptides including their purification by HPLC and analysis using ESI-MS or MALDI-TOF. Methods of cyclization are described by Bulaj G and Olivera B M, 2008, Antioxid Redox Signal, 10 (1):141-55, and Amit M et al, 2009. Biochemistry, 48 (15):3288-3303. These procedures are also useful for peptides containing two or more disulfide bonds Linkers Coupled to Peptides Cyclic or linear stereoisomer peptides may be coupled to a linker during peptide synthesis or the linker may be coupled to a branch of an activated polymer via conjugation. A linker conjugated to a chemical functional group of a branch of a polymer is useful to determine the cellular transport, clearance, cleavage or release of the linked peptide into the target tissue, cell or sub-cellular location and can serve as initiation site that enables binding to one or more other molecular moieties. The addition of linkers is achieved by synthesis methods well established in the art. The linker may contain two or more amino acids preferably selected from Lys, Gly, Phe, Leu, Ser but other amino acids such as Tyr, Glu, Gln and Asn can also be chosen and with groups suitable for attachment to the target functional groups of a polymer, either pre-activated or in the presence of a suitable coupling reagent. Each amino acid with a functional group may be reacted with one side branch of the target pre-activated polymer.

Polymers

Polymers used to create compounds to deliver drugs to tissues, cells or cellular compartments such as the cytosol, include polylactide, polyglycolic acid (PGA), polylactic acid (PLA), polyhydroxy acids (PHAs), poly lactic-co-glycolic acid (PLGA), polyethylene Glycol (PEG), and branched PEG, polyvinyl acetate, polyvinyl alcohol, α, β, poly (N-hydroxyetheyl)-DL-aspartamide (PHEA), α, β, poly (N-hydroxypropyl)-DL-aspartamide (PHPA), poly-N-(2-Hydroxypropyl)methacrylamide (HPMA), and HPMA copolymers, polyethylenimine (PEI), polylysine and derivatives thereof. Polylactide and poly lactic-co-glycolic acid (PLGA) are typically used to provide sustained drug delivery for a determined period. Poly(lactic acid) and polyethylene glycol are suitable for controlled parenteral drug delivery system. Other delivery systems may include liposome based-drug delivery carriers, nano-particles based on di-stearoyl phosphatidyl choline (DSPC), cholesterol, dioleoyl phosphatidyl ethanolamine (DOPE), and di-stearoyl phosphatidyl ethanolamine (DSPE)-mPEG2000 conjugated to the target molecule. Peptides, polypeptides and proteins have been conjugated to polyethylene glycol (PEG) as delivery system to tissues or cells with the purpose of improving the activity of conjugated molecules reducing significantly their toxicity. In this invention the preferred polymer is N-(2-Hydroxypropyl)methacrylamide) or HPMA and HPMA copolymers. The compounds created with poly N-(2-Hydroxypropyl)methacrylamide) or HPMA comprise different stereoisomer peptides and a peptide-ligand that are independently bound to a functional group of a separate branch of the polymer scaffold via degradable and non-degradable linkers, respectively, creating novel ligand-targeted multi stereoisomer peptide-polymer conjugate compounds. These compounds can be formulated for different administration routes and used in the anti-diseases strategies described here.

Preparation of compounds of the general formula (Pol-$L_1$-sP)$_n$-Pol-$L_2$-s$P_L$ Description and methods of preparation of these compounds are described in non-provisional U.S. patent application Ser. No. 12/836187 and PCT/US 10/41982, each of which is herein incorporated by reference in its entirety.

(1) HPMA Polymer and Stereoisomer-peptide-HPMA Conjugates

Polymers have been used to deliver drugs to tissues or cells. They include polylactide (PL), poly lactic-co-glycolic acid (PLGA), polyethylene glycol (PEG) and poly-N-(2-Hydroxypropyl) methacrylamide (HPMA) to create peptide-polymer conjugates. In an embodiment of this invention, the preferred polymer is N-(2-Hydroxypropyl) methacrylamide (HPMA), which is a biocompatible linear scaffold polymer carrier with separate branches where individual molecules, e.g., stereoisomer peptides, can be conjugated to functional groups of a polymer branch. The function of the HPMA polymer is to deliver the peptides in the form of a conjugate to targeted tissues, cells, and sub-cellular locations. The polymer conjugate compounds may contain one or several different synthetic linear or cyclic stereoisomer peptides that may be independently attached each to a functional group of a separate branch of a polymer scaffold via a linker to create novel synthetic linear and cyclic multi-targeted stereoisomer peptide polymer conjugate compounds. HPMA polymer has been used to covalently conjugating low molecular weight drugs to increase its therapeutic effect. The selection of HPMA relies on its extensive research, well-known chemical and structural properties, and their suitability as carriers for drug delivery, especially with toxic anti-cancer molecules, in many clinical applications (U.S. Pat. No. 5,037,883; Kopecek, et al, Eur. J. Pharm. Biopharm., 2000, 50: 61-81; Vicent M J et al. 2008. Expert Opin Drug Deliv. 5(5):593-614; Greco F and Vicent M J. 2008. Front Biosci. 2008 13:2744-56). HPMA has been conjugated to a variety of small inorganic molecules, antibodies, antibiotics, natural proteins, and immunoglobulin, has shown to extend the molecules half-life in vivo, and/or reduce significantly their immunogenicity, antigenicity and toxicity, and to enhance their biological activity, prolong blood circulation time, and increase aqueous solubility, and resistance to protease digestion. The polymer, HPMA, is inert, safe, non-toxic, non-immunogenic, water soluble, and biocompatible.

(2) Synthesis of Co-polymers and Polymer Conjugates

In general, the side chains of HPMA copolymer with terminal $NH_2$ groups, are synthesized by radical polymerization using AIBN (2,2'-azobisisobutyronitrile) as the initiator in the presence of oxidants such as DMSO and gas argon. After polymerization, the HPMA copolymer is purified to obtain a polymer of the desired molecular weight, and is used to conjugate the target molecules, which in this invention refer to stereoisomer peptides. HPMA may be conjugated to the stereoisomer peptide via a linker preferably containing the amino acids Lysine (Lys), Glycine (Gly), Phenylalanine (Phe) and Leucine (Leu), to the epsilon-amino group of Lys residue, or to the alpha-amino group of a residue in the peptide.

In embodiments of this invention, HPMA copolymers are synthesized by free-radical precipitation copolymerization of comonomers in 10% v/v dimethyl sulfoxide (DMSO) in acetone using N,NV-azobisisobutyronitrile (AIBN) as the initiator. The copolymer is sealed in an ampoule under nitrogen and stirred at 50° C. for 24 hours. The precipitated copolymeric precursor is dissolved in methanol and reprecipitated in acetone/ether (3:1) to obtain the pure product. The HPMA copolymer-stereoisomer peptide-polymer conjugates are synthesized via p-nitrophenyl ester aminolysis of the polymeric precursor Peptide(s) are dissolved in dry N,N-DMF under constant stirring; then dry pyridine (1:1 molar equivalents relative to the polymeric ONp content) followed by polymeric precursor in dry DMF is added to the peptide(s) solution (1.3 times excess molar equivalents). The reaction mixture is bubbled with nitrogen and continuously stirred at room temperature for 22 hours at 50° C. The reaction is terminated with 1-amino-2-propanol. The crude conjugate is dialyzed against deionized water and lyophilized. The peptide content in the conjugate is analyzed by amino acid analysis, and the molecular weight of the conjugate is estimated by size exclusion chromatography, which may be between about 30 to 50 Kda. The term "about" indicates that in preparations of HPMA, some molecules will weigh more, some less, than the stated molecular weight. The actual weight will depend on the polymerization reaction that determines the number of branches desired in the polymer and the linker and the number of amino acids comprising the linker.

Conjugation of stereoisomer peptides to the polymer can also be carried out by using HPMA containing a carboxyl-terminated linker (2, 3 or 4 amino acids) that has been pre-activated as the para-nitrophenol ester (ONp). The stereoisomer peptides are prepared in partially protected form for use in coupling to the pre-activated HPMA carrying the linker. Each different stereoisomer peptide is conjugated separately to the amino acid residue attached to the activated copolymer via the free N-terminal amino group of the stereoisomer peptide or in mixtures using an appropriate polymer-peptide ratio. Briefly, the peptide is conjugated to the copolymer via p-nitrophenyl ester aminolysis of the polymeric precursor. Each D-peptide is dissolved separately in dry N,N-DMF, and under constant stirring, dry diisopropylethylamine (DIEA) followed by polymeric precursor also in dry DMF are added to the peptide(s) solution. The reaction mixture is stirred at ambient temperature for 2-24 hours, and the reaction terminated with 1-amino-2-propanol. For stereoisomer peptide conjugates containing side-chain amino acid protecting groups, the crude protected conjugate is isolated by precipitation in diethyl ether and centrifugation. The residual precipitate undergoes final deprotection of side-chain amino acid protecting groups by hydrolysis in 95% TFA/water with appropriate scavenger (e.g. TIPS [triisopropylmethylsilane]). The crude conjugate is isolated by precipitation in diethyl ether and subsequent centrifugation. For unprotected peptide conjugates, the crude conjugate is isolated by dialysis against deionized water and lyophilization. The resulting polymer conjugates are resuspended in water and then purified by FPLC. The peptide content in the conjugate is analyzed by amino acid analysis. Conjugate molecular weight is determined by size exclusion chromatography and absorption is monitored at 215 nm for peptide bonds and 280 nm for aromatics. The polymer has a molecular weight no greater than 80 kDa. Most preferably, the polymer has a molecular weight in the range of 20 kDa to 50 kDa.

Use of Synthetic Stereoisomer Peptides of the Present Invention

The collection of peptides comprising the stereoisomer peptide compounds of the present invention are useful in assays in vitro to determine their inhibitory activities ($IC_{50}$) in different human endothelial cell lines and other human cells and in strains of a desired target pathogen. In the preferred practice of the present invention, different synthetic stereoisomer peptides are advantageously incorporated in the polymer system. Thus, the polymer to which the peptides and peptide-ligand of the present invention are conjugated is hydrophilic HPMA. This peptide-polymer combination system creates novel synthetic ligand-targeted stereoisomer peptide-polymer conjugates. These polymer conjugates are compounds that provide benefits over non-conjugated polymers, such as improved solubility and in vivo stability. These conjugates can be used to determine the polymer's transport properties, efficiency of internalization, permeability, and retention and biodistribution in vitro in certain human cells or in vivo in a particular disease animal model, or its binding or internalization in different, viral or bacterial cells. The stereoisomer peptides conjugated to the polymer have the potential to block or inhibit functional domains of corresponding target proteins; these compounds can be used as reagents for determining the peptides biodistribution in the appropriate human cells in vitro, as well as in vivo in appropriate animal models to treat a disease. By labeling such compounds with $^{99m}Tc$ or $^{90}Y$ or using fluorescent molecules, one can identify cells having the compounds on their surfaces or in subcellular locations. In addition, the stereoisomer peptides and the compounds can be used in Western blotting, ELISA (enzyme-linked immunosorbent assay), FACS analysis based on their ability to bind specifically to the target proteins or cells; the stereoisomer peptides may be also used in purifying cells expressing a particular microorganism protein on the cell surface or inside the cells.

The stereoisomer peptides in free from are also useful as commercial reagents for various research and diagnostic applications including but not limited to antigen-antibody binding and complexes formation using commercially available pathogen or proteins antibodies. They could also be used as blocking reagents in random peptide screening aimed to find new antigens that target a specific causing disease protein or an uncommon microorganism strain, or to raise antibodies specific for a particular protein of human or microorganisms.

Pharmaceutical Compositions

The invention further provides pharmaceutical compositions comprising formulated linear and cyclic stereoisomer peptide compounds and multi stereoisomer peptide-polymer conjugate compounds. The compounds may be prepared for administration by oral, transmucosal (nasal, vaginal, rectal, or sublingual), parenteral (intramuscular, intraperitoneal, intravenous (IV) or subcutaneous injection), topical, transdermal (passively) and pulmonary routes, and may be formulated in dosage forms appropriate for each route of administration using pharmaceutically acceptable excipients.

In general, comprehended by the invention the pharmaceutical compositions comprise effective amounts of a stereoisomer peptide, a mixture of stereoisomer peptides or stereoisomer peptide-polymer conjugates, together with pharmaceutically acceptable diluents, solubilizers, emulsifiers, preservatives, adjuvants and/or carriers. Such compositions may include diluents of various buffer content, pH and ionic strength; additives such as detergents and solubilizing agents, anti-oxidants, preservatives and bulking substances, and the compositions may be prepared in liquid form or in dried powder form. Procedures to prepare pharmaceutical compositions are well known in the art. Martin EW, 1990, Remington's Pharmaceutical Sciences. 8th Ed. Mack Publishing Co., Easton, Pa. 18042, is herein incorporated by reference.

Oral Delivery

In preferred embodiments, the peptide compounds of this invention are synthetic stereoisomer or chiral peptides, which unlike typical peptide formulations with L-peptides, have the advantage of not being degraded by proteases; are very stable, and have enhanced pharmaceutical properties for oral bioavailability or for administration in harsh environments via the mucosa. Natural peptides with L amino acids degrade very fast and thus do not allow such routes of administration. In particular, cyclic stereoisomer peptides containing D- and L-amino acids or only D-amino acids are effective therapeutics due to enhanced stability. Thus, they can be orally administered to an organism, and are readily taken up and delivered to the serum. These modifications facilitate their uptake into the blood stream from the digestive/intestine system. In preferred embodiments, linear and cyclic stereoisomer peptides are conjugated to a biocompatible polymer further enhancing their bioavailability and therefore can be administered orally, without protection against proteolysis by stomach acid. The peptides, comprising the active material, are stable at low pH and resistant to degradation by enzymes. Generally, the chemical modification contemplated here permits stability of the components and inhibition of proteolysis by enzymes of the digestive tract, as well as increased overall circulation time in the body.

A description of solid dosage forms is given by Marshall K, 1979, In Modern Pharmaceutics, Edited by G. S. Banker and C. T. Rhodes Chapter 10, 197 herein incorporated by reference. In general, the formulation will include inert ingredients, which allow for protection against the digestive system environment, and release of the biologically active material in the intestine, and blood stream. Also contemplated for use herein are liquid dosage forms for oral administration, including emulsions, solutions, suspensions, and syrups, which may contain other components. A coating impermeable to acid pH, may be considered to ensure full gastric resistance. Examples of inert ingredients used as enteric coatings are polyvinyl acetate phthalate, and their derivatives. Capsules may consist of a hard shell for delivery of dry therapeutic (i.e. powder), for liquid forms, a soft gelatin shell may be used. Colorants and/or flavoring agents, and diluents may also be included. Certain inorganic salts may be used as fillers. Disintegrants may be included in the formulation as well as binders to hold the compounds together to form a tablet and may include starch and gelatin. The unique properties of the compounds of this invention, allows flexibility in the mode of administration in addition to their potential for oral bioavailability.

Mucosal Delivery: Nasal, Vaginal, and Rectal Administration

Compositions for nasal, rectal, and vaginal delivery of the compounds of this invention are also contemplated. A therapeutic drug must be formulated to effectively penetrate the mucosa via these routes and target the earliest events of a disease or a pathogenic infection. Nasal delivery, for example, allows the passage of compounds to the blood stream directly after administering the therapeutic product to the nose, without the necessity for deposition of the product in the lung. Formulations for nasal delivery include those with dextran or cyclodextran and excipients well known in the art. Compositions for rectal or vaginal administration are preferably suppositories, which may contain, in addition to the active substance, excipients such as cocoa butter or wax, and may include lubricants made of wax or oil. Since the compounds of this invention resist degradation by enzymes found in human blood, serum, and body secretions, flexibility in the mode of administration as a topical viral prophylactic for harsh mucosal environments is possible. Natural peptides with L-amino acids do not allow such routes of administration given their high instability.

Topical Drug Delivery

Formulations for topical drug delivery include ointments and creams. Ointments are semisolid preparations, based on petrolatum or other petroleum derivatives. Creams containing the active ingredient include viscous liquid or semisolid emulsions. Cream bases are typically water-washable, and contain an oil phase, an emulsifier, and an aqueous phase. The oil phase is generally comprised of petrolatum and a fatty alcohol such; the aqueous phase generally contains a humectant. The emulsifier in a cream formulation is generally a nonionic, anionic, cationic, or amphoteric surfactant. The specific ointment or cream base to be used as will be appreciated by those skilled in the art is one that will provide for optimum drug delivery. As with other carriers or vehicles, an ointment base should be inert, stable, nonirritating and nonsensitizing.

Parenteral Delivery

Preparations for parenteral administration are also contemplated here and are well known in the art. They include standard sterile aqueous or non-aqueous solutions, suspensions, or emulsions. Examples of non-aqueous solvents or vehicles are polyethylene glycol, propylene glycol, vegetable oils, such as olive oil and corn oil, gelatin, and injectable organic esters such as ethyl oleate. Such dosage forms may also contain preserving, wetting, emulsifying, and dispersing agents. These formulations are sterilized by filtration by incorporating sterilizing agents into the compositions, by irradiating the compositions, or by heating the compositions. They can also be manufactured using injectable sterile water, or sterile medium, immediately before use.

Pulmonary Delivery

Compounds of this invention can also be delivered to the lungs by inhaling and traverses across the lung epithelial lining to the blood stream. A wide range of mechanical devices designed for pulmonary delivery of therapeutic products are commercially available including but not limited to nebulizers, metered dose inhalers, and powder inhalers, all of which are familiar to those skilled in the art. Such devices require appropriate formulations suitable for the dispensing of compounds.

The foregoing formulations and administration methods are intended to be illustrative and not limiting. It will be appreciated that using the teaching provided herein, other suitable formulations and modes of administration could be readily devised and applied to the stereoisomer peptide compounds and stereoisomer peptide-polymer conjugate compounds of this invention.

Dosages

For all of the stereoisomer peptide compounds and stereoisomer peptide-polymer conjugate compounds, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends on the desired therapeutic effect, on the route of administration, and on the duration of the treatment desired. Generally, dosage levels of 0.001 to 10 mg/kg of body weight daily are administered to mammals. Physicians may initially use escalating dosages starting at a concentration that meet the requirements for each individual being treated.

Modifications and variations of the compositions of the present invention, and methods for use, will be obvious to those skilled in the art from the foregoing detailed descriptions. Such modifications and variations are intended to fall within the scope of the appended claims. The references cited here and throughout the entire specification are provided merely to clarify and illustrate the description of the present invention and is not an admission that any such reference is "prior art" to the present invention. The novel compounds described in the specification can be further tested by confirming their specific inhibitory effects in their corresponding target proteins using appropriate in vitro assays and in vivo, animal models.

Treatment of Mammalian Diseases

The conjugates of the invention are useful in the treatment of a variety of mammalian disease conditions and disorders. Examples of such diseases in human patients are abnormal angiogenesis, pathological conditions of the eye including age-related macular degeneration, choroidal neovascularization and diabetic retinopathy, cancer, solid tumors, tumor metastasis, inflammatory diseases, Alzheimer's and Parkinson's diseases, atherosclerosis, cardiovascular diseases, multiple sclerosis, autoimmune diseases, diabetes, rheumatoid arthritis, stroke, neurological disorders, dementia, brain disorders, neurodegenerative disorders, neuropsychiatric illnesses, bipolar disorder, diseases caused by aging, and HIV/AIDS, and other pathogen agent infections including but not limited to prions, viruses, bacteria, fungi, and parasites.

Various available disease models can be used to experimentally studying these diseases in vivo. For example, animal models include but are not limited to mouse models for macular degeneration, for breast, pancreatic, melanoma and other cancers, for multiple sclerosis, and for neuropathies to name a few.

EXAMPLES

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

Example 1

Figure 2:
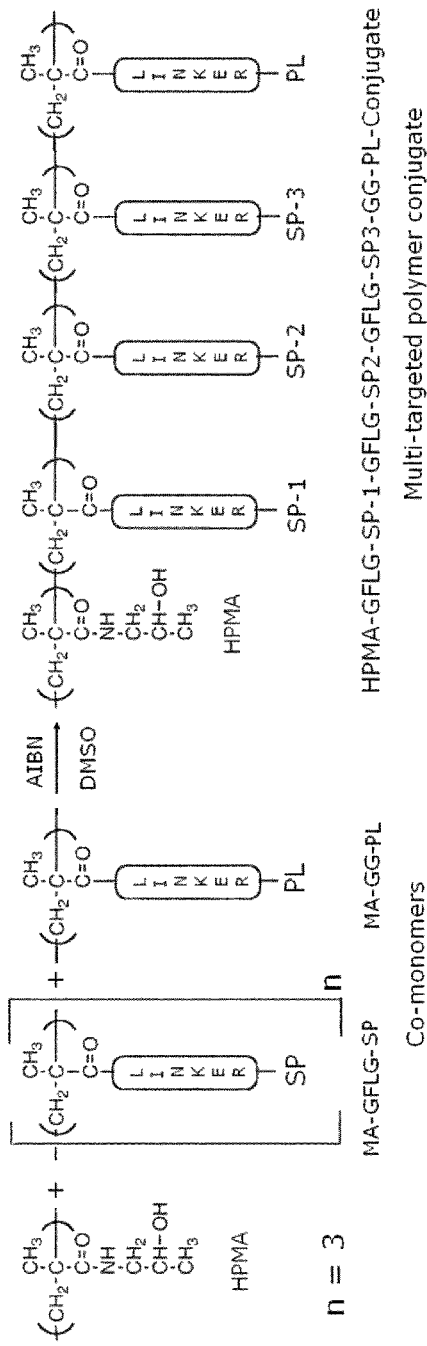
FIG. 2 illustrates the ligand-targeted HPMA-GFLG-D-Peptide-1-GFLG-D-Peptide-2-GFLG-D-Peptide-3-GG-Peptide-Ligand-conjugate created by radical polymerization of a mixture of three different stereoisomer peptides co-monomers and a synthetic peptide-ligand co-monomer in the presence of excess of polymer N-2(Hydroxypropyl)methacrylamide or HPMA.

Synthesis of a Ligand-targeted Multi-stereoisomer Peptide-polymer Conjugate Compound The synthesis of this compound comprises three MA-GFLG-D-peptide monomers each with a different D-peptide, and MA-GG-PL monomer with a peptide-ligand (PL). These monomers are copolymerized to create a multi-stereoisomer peptide-polymer conjugate compound of the form HPMA-GFLG-D-peptide-1-GFLG-D-peptide-2-GFLG-D-peptide-3-GG-PL (FIG. 2). The pre-activated monomer precursors MA-GFLG-ONp and MA-GG-ONp containing ONp groups are prepared by adding to a solution of MA-GFLG-OH or Ma-GG-OH in 80 ml of DMF, a solution of p-nitrophenol in 20 ml of DMF under stifling and cooling to −10° C., followed by a solution of DCC in 8 ml of DMF. The two separate reaction mixtures are stirred for six hours at −10° C., and then overnight at 4° C. The precipitated by product is filtered off and the DMF removed by evaporation. The residue is dissolved in EtOAc and the remaining byproduct is filtered off. EtOAc is evaporated and the final product is soaked in ether to remove excess p-nitrophenol. This procedure is repeated three times. Purity of MA-GFLG-ONp or MA-GG-ONp is checked by calculating the extinction coefficient in DMSO. MA-GFLG-ONp or MA-GG-ONp content is assessed by UV spectrophotometry by release of p-nitrophenol from the polymer in 1N NaOH.

Coupling D-peptides or the peptide-ligand (PL) to the activated para-nitrophenyl ester group in the linker (created by reaction of the carboxyl groups of a Gly residue, and conversion to p-nitrophenyl esters), is carried out via D-peptide amino groups by nucleophilic attack at the reactive ester groups forming amide linkages (covalent bonds) between the reactive p-nitrophenyl ester groups of the linker and the alpha-amino group of amino acids or the epsilon-amino group of a Lys residue in the D-peptide. Alternatively, for cyclic peptides, coupling to the linker is carried out via the epsilon-amino group of a terminal Lys residue in the D-peptide.

Coupling peptides to the monomer precursors MA-GFLG-ONp or MA-GG-ONp is carried out in separate reactions for each different D-peptide and PL. The copolymer precursor and D-peptide or PL are dissolved in DMF; N,N-diisopropylethylamine (DIPEA) diluted in DMF (1:1, v:v) is added slowly dropwise while stifling the mixture at room temperature in the dark overnight. The reactive ester groups (i.e., carboxyl groups of residues converted to p-nitrophenyl ester) of the pre-activated monomer MA-GFLG-ONp or MA-GG-ONp are reacted with the D-peptide or the PL respectively, via nucleophilic attack of the amino groups forming amide linkages with the linker. Unreacted ONp groups are deactivated (hydrolyzed) with 1-amino-2-propanol, the mixture containing the final product MA-GFLG-D-peptide or MA-GG-PL is diluted in deionized water. Each separate monomer solution is dialyzed and then lyophilized. For a polymer compound with three different D-peptides and one PL, four separate reactions are prepared. The exact content of PL or D-peptide in a particular monomer is determined by standard amino acid analysis. Polymerization of the three monomers with different D-peptides and one peptide-ligand (PL) to obtain the final product is carried out by copolymerization of HPMA with the monomers MA-GFLG-D-peptide-1, MA-GFLG-D-peptide-2, MA-GFLG-D-peptide-3, and MA-GG-PL in acetone in the presence of AIBN as initiator; HPMA and monomers are reacted at a ratio 10:1 respectively. Briefly, radical precipitation copolymerization is carried out using a mixture of the above monomers at various molar ratios using the initiator 2,2'-azobisisobutironitrile (AIBN) and DMSO. The solution containing excess HPMA and monomers in acetone is mixed with the initiator, transferred to an ampoule, bubbled with nitrogen for 5 min, and sealed and placed in an oil bath at 50° C. for 24 hours under stirring. After 24 hours the copolymers would precipitate out of solution and the ampoules are cooled to room temperature and placed in the freezer for 20 minutes to increase the yield of the precipitated polymer further. The copolymers are filtered off, dissolved in methanol, and precipitated in ether. After filtration and washing with ether, the polymer is dried under vacuum. The ligand-targeted stereoisomer peptide polymer conjugate (see FIG. 2) in purified form is analyzed by HPLC. These compounds can be experimentally evaluated using in vitro and in vivo assays to determine their ability to inhibit or block the activity of particular target proteins.

Example 2

Synthesis of Polymer Conjugates Using Preactivated Monomer

Preactivated HPMA-GFLG-ONp can be obtained directly from the supplier reducing the number of synthesis steps. Each different D-peptide is coupled by its terminal amino group to the active ONp group via nucleophilic attack in separate reactions to synthesize co-polymers carrying each a different D-peptide attached to a linker as described in example 2. For example, four copolymers are first synthesized, three copolymers with a different synthetic stereoisomer peptide (SSP) and one with a peptide-ligand (PL). Then all the separate copolymers, including HPMA-GG-PL can be copolymerized in excess of HPMA (10×) by radical copolymerization in the presence of the initiator AIBN, DMSO and $N_2$ gas to obtain ligand-targeted HPMA-GG-LP-GFLGD-peptide-1-GFLG-D-peptide-2-GFLG-D-peptide-3 polymer conjugate. This compound has a general formula SPn-L1-PL-L2. SP can be independently selected from the collection of peptides SEQ ID NO 1 through SEQ ID NO 152 disclosed in file Gonzalez_Sequence_Listing_October_28_2010.txt but selecting from any one of the different groups of peptides that specifically target the functional domains of proteins involved in a particular disease.

The foregoing invention has been described in detail by way of description, illustration, and example, for the purpose of clarity of understanding. One skilled in the art will easily ascertain that certain modifications and variations of the compositions of the present invention, maybe practiced without departing from the spirit and scope of the appended claims.

---

What is claimed is:

1. A ligand-targeted multi-stereoisomer peptide polymer conjugate compound represented by a formula $(Pol-L_1-sP)_n-Pol-L_2-sP_L$, wherein:
   Pol is HPMA, HPMA copolymer, or HPMA derivatives,
   $L_1$ is a degradable linker with one end conjugated to a polymer branch and the other end conjugated to a stereoisomer peptide, comprising Gly, Phe, Leu, and Gly amino acids,
   sP is stereoisomer peptide of SEQ ID NO:10, 34, 47, 97, and 101,
   n is an integer from 2 to 5 representing different peptides, said peptides target the functional domains of proteins, said proteins are EGFR, HSP90, pl3K, neuropilin-2 (NPR-2), and αvβ3,
   $L_2$ is non-degradable linker with one end conjugated to a polymer branch and the other end conjugated to stereoisomer peptide-ligand comprising Gly, Gly amino acids,
   $sP_L$ is stereoisomer peptide-ligand comprising SEQ ID NO:25 or SEQ ID NO:112.

2. The ligand-targeted multi-stereoisomer peptide polymer conjugate compound of claim 1, wherein said stereoisomer is a peptide made of D-amino acids, inversed or retro-inversed, and linear or cyclic.

3. The ligand-targeted multi-stereoisomer peptide polymer conjugate compound of claim 2, wherein cyclic stereoisomer peptide is cyclized via disulfide bond, amide bond or thio-ether bond.

4. The ligand-targeted multi-stereoisomer peptide polymer conjugate compound of claim 1, wherein said stereoisomer peptide-ligand is high affinity peptide, cell penetrating peptide, or transport peptide.

5. A composition comprising a compound as claimed in claim 1 and an acceptable diluent, solubilizer, emulsifier, preservative, adjuvant and/or carrier, wherein said composition is administered by the oral, parenteral, topical, pulmonary, mucosal, or transdermal route.

* * * * *

SEQUENCE LISTING

```
<160> NUMBER OF SEQ ID NOS: 152

<210> SEQ ID NO 1
<211> LENGTH: 28
<212> TYPE: PRT
<213> ORGANISM: Artificial sequence
<220> FEATURE:
<223> OTHER INFORMATION: Cyclic peptide and D-peptide analogs

<400> SEQUENCE: 1

Cys Gln Gly Thr Ser Asn Lys Leu Thr Gln Leu Gly Thr Phe Glu Asp
1               5                   10                  15

His Phe Leu Ser Leu Gln Arg Met Phe Asn Asn Cys
            20                  25

<210> SEQ ID NO 2
<211> LENGTH: 31
<212> TYPE: PRT
<213> ORGANISM: Artificial sequence
<220> FEATURE:
<223> OTHER INFORMATION: Cyclic peptide and D-peptide analogs

<400> SEQUENCE: 2

Cys Asn Val Glu Ser Ile Gln Trp Arg Asp Ile Val Ser Ser Asp Phe
1               5                   10                  15

Leu Ser Asn Met Ser Met Asp Phe Gln Asn His Leu Gly Ser Cys
            20                  25                  30

<210> SEQ ID NO 3
<211> LENGTH: 18
<212> TYPE: PRT
<213> ORGANISM: Artificial sequence
<220> FEATURE:
<223> OTHER INFORMATION: Cyclic peptide and D-peptide analogs

<400> SEQUENCE: 3

Cys Asp Pro Ser Cys Pro Asn Gly Ser Cys Trp Gly Ala Gly Glu Glu
1               5                   10                  15

Asn Cys

<210> SEQ ID NO 4
<211> LENGTH: 17
<212> TYPE: PRT
<213> ORGANISM: Artificial sequence
<220> FEATURE:
<223> OTHER INFORMATION: Cyclic peptide and D-peptide analogs
```

-continued

```
<400> SEQUENCE: 4

Cys Ala Gln Gln Cys Ser Gly Arg Cys Arg Gly Lys Ser Pro Ser Asp
1               5                   10                  15

Cys

<210> SEQ ID NO 5
<211> LENGTH: 17
<212> TYPE: PRT
<213> ORGANISM: Artificial sequence
<220> FEATURE:
<223> OTHER INFORMATION: Cyclic peptide and D-peptide analogs

<400> SEQUENCE: 5

Cys His Asn Gln Cys Ala Ala Gly Cys Thr Gly Pro Arg Glu Ser Asp
1               5                   10                  15

Cys

<210> SEQ ID NO 6
<211> LENGTH: 10
<212> TYPE: PRT
<213> ORGANISM: Artificial sequence
<220> FEATURE:
<223> OTHER INFORMATION: Cyclic peptide and D-peptide analogs

<400> SEQUENCE: 6

Cys Arg Lys Phe Arg Asp Glu Ala Thr Cys
1               5                   10

<210> SEQ ID NO 7
<211> LENGTH: 28
<212> TYPE: PRT
<213> ORGANISM: Artificial sequence
<220> FEATURE:
<223> OTHER INFORMATION: Cyclic peptide and D-peptide analogs

<400> SEQUENCE: 7

Cys Pro Pro Leu Met Leu Tyr Asn Pro Thr Thr Tyr Gln Met Asp Val
1               5                   10                  15

Asn Pro Glu Gly Lys Tyr Ser Phe Gly Ala Thr Cys
            20                  25

<210> SEQ ID NO 8
<211> LENGTH: 13
<212> TYPE: PRT
<213> ORGANISM: Artificial sequence
<220> FEATURE:
<223> OTHER INFORMATION: Cyclic peptide and D-peptide analogs

<400> SEQUENCE: 8

Cys Pro Arg Asn Tyr Val Val Thr Asp His Gly Ser Cys
1               5                   10

<210> SEQ ID NO 9
<211> LENGTH: 16
<212> TYPE: PRT
<213> ORGANISM: Artificial sequence
<220> FEATURE:
<223> OTHER INFORMATION: Cyclic peptide and D-peptide analogs

<400> SEQUENCE: 9

Cys Gly Ala Asp Ser Tyr Glu Met Glu Glu Asp Gly Val Arg Lys Cys
1               5                   10                  15

<210> SEQ ID NO 10
<211> LENGTH: 5
```

```
<212> TYPE: PRT
<213> ORGANISM: Artificial sequence
<220> FEATURE:
<223> OTHER INFORMATION: D-peptide and analogs

<400> SEQUENCE: 10

Cys Val Pro Trp Cys
1               5

<210> SEQ ID NO 11
<211> LENGTH: 23
<212> TYPE: PRT
<213> ORGANISM: Artificial sequence
<220> FEATURE:
<223> OTHER INFORMATION: Cyclic peptide and D-peptide analogs

<400> SEQUENCE: 11

Cys Gly Ala Asp Ser Tyr Glu Met Glu Glu Asp Gly Val Arg Lys Cys
1               5                   10                  15

Lys Lys Cys Glu Gly Pro Cys
            20

<210> SEQ ID NO 12
<211> LENGTH: 26
<212> TYPE: PRT
<213> ORGANISM: Artificial sequence
<220> FEATURE:
<223> OTHER INFORMATION: Cyclic peptide and D-peptide analogs

<400> SEQUENCE: 12

Cys Asn Gly Ile Gly Ile Gly Glu Phe Lys Asp Ser Leu Ser Ile Asn
1               5                   10                  15

Ala Thr Asn Ile Lys His Phe Lys Asn Cys
            20                  25

<210> SEQ ID NO 13
<211> LENGTH: 30
<212> TYPE: PRT
<213> ORGANISM: Artificial sequence
<220> FEATURE:
<223> OTHER INFORMATION: Cyclic peptide and D-peptide analogs

<400> SEQUENCE: 13

Cys Tyr Ala Asn Thr Ile Asn Trp Lys Lys Leu Phe Gly Thr Ser Gly
1               5                   10                  15

Gln Lys Thr Lys Ile Ile Ser Asn Arg Gly Glu Asn Ser Cys
            20                  25                  30

<210> SEQ ID NO 14
<211> LENGTH: 18
<212> TYPE: PRT
<213> ORGANISM: Artificial sequence
<220> FEATURE:
<223> OTHER INFORMATION: Cyclic peptides and D-peptide analogs

<400> SEQUENCE: 14

Cys His Ala Leu Cys Ser Pro Glu Gly Cys Trp Gly Pro Glu Pro Arg
1               5                   10                  15

Asp Cys

<210> SEQ ID NO 15
<211> LENGTH: 10
<212> TYPE: PRT
<213> ORGANISM: Artificial sequence
<220> FEATURE:
<223> OTHER INFORMATION: Cyclic peptide and D-peptide analogs
```

```
<400> SEQUENCE: 15

Cys Arg Asn Val Ser Arg Gly Arg Glu Cys
1               5                   10

<210> SEQ ID NO 16
<211> LENGTH: 17
<212> TYPE: PRT
<213> ORGANISM: Artificial sequence
<220> FEATURE:
<223> OTHER INFORMATION: Cyclic peptide and D-peptide analogs

<400> SEQUENCE: 16

Cys Asn Leu Leu Glu Gly Glu Pro Arg Glu Phe Val Glu Asn Ser Glu
1               5                   10                  15

Cys

<210> SEQ ID NO 17
<211> LENGTH: 22
<212> TYPE: PRT
<213> ORGANISM: Artificial sequence
<220> FEATURE:
<223> OTHER INFORMATION: Cyclic peptide and D-peptide analogs

<400> SEQUENCE: 17

Cys His Pro Glu Cys Leu Pro Gln Ala Met Asn Ile Thr Cys Thr Gly
1               5                   10                  15

Arg Gly Pro Asp Asn Cys
            20

<210> SEQ ID NO 18
<211> LENGTH: 10
<212> TYPE: PRT
<213> ORGANISM: Artificial sequence
<220> FEATURE:
<223> OTHER INFORMATION: Cyclic peptide and D-peptide analogs

<400> SEQUENCE: 18

Cys Ala His Tyr Ile Asp Gly Pro His Cys
1               5                   10

<210> SEQ ID NO 19
<211> LENGTH: 23
<212> TYPE: PRT
<213> ORGANISM: Artificial sequence
<220> FEATURE:
<223> OTHER INFORMATION: Cyclic peptide and D-peptide analogs

<400> SEQUENCE: 19

Cys Pro Ala Gly Val Met Gly Glu Asn Asn Thr Leu Val Trp Lys Tyr
1               5                   10                  15

Ala Asp Ala Gly His Val Cys
            20

<210> SEQ ID NO 20
<211> LENGTH: 17
<212> TYPE: PRT
<213> ORGANISM: Artificial sequence
<220> FEATURE:
<223> OTHER INFORMATION: Cyclic peptide and D-peptide analogs

<400> SEQUENCE: 20

Cys His Pro Asn Cys Thr Tyr Gly Cys Thr Gly Pro Gly Leu Glu Gly
1               5                   10                  15

Cys
```

```
<210> SEQ ID NO 21
<211> LENGTH: 7
<212> TYPE: PRT
<213> ORGANISM: Artificial sequence
<220> FEATURE:
<223> OTHER INFORMATION: Cyclic peptide and D-peptide analogs

<400> SEQUENCE: 21

Cys Arg Leu Leu Gly Ile Cys
1               5

<210> SEQ ID NO 22
<211> LENGTH: 22
<212> TYPE: PRT
<213> ORGANISM: Artificial sequence
<220> FEATURE:
<223> OTHER INFORMATION: Cyclic peptide and D-peptide analogs

<400> SEQUENCE: 22

Cys Leu Leu Asp Tyr Val Arg Glu His Lys Asp Asn Ile Gly Ser Gln
1               5                   10                  15

Tyr Leu Leu Asn Trp Cys
            20

<210> SEQ ID NO 23
<211> LENGTH: 12
<212> TYPE: PRT
<213> ORGANISM: Artificial sequence
<220> FEATURE:
<223> OTHER INFORMATION: Cyclic peptide and D-peptide analogs

<400> SEQUENCE: 23

Cys Ser Leu Leu Gly Gly Arg Leu Leu Gly Gln Cys
1               5                   10

<210> SEQ ID NO 24
<211> LENGTH: 10
<212> TYPE: PRT
<213> ORGANISM: Artificial sequence
<220> FEATURE:
<223> OTHER INFORMATION: Cyclic peptides and D-peptide analogs

<400> SEQUENCE: 24

Cys Ile Asp Arg Asn Gly Leu Gln Ser Cys
1               5                   10

<210> SEQ ID NO 25
<211> LENGTH: 7
<212> TYPE: PRT
<213> ORGANISM: Artificial sequence
<220> FEATURE:
<223> OTHER INFORMATION: Cyclic peptide and D-peptide analogs

<400> SEQUENCE: 25

Cys Phe Asn Gly Arg Asp Cys
1               5

<210> SEQ ID NO 26
<211> LENGTH: 12
<212> TYPE: PRT
<213> ORGANISM: Artificial sequence
<220> FEATURE:
<223> OTHER INFORMATION: Linear peptide and D-peptide analogs

<400> SEQUENCE: 26

His Glu Val Val Lys Phe Met Asp Val Tyr Gln Arg
```

```
<210> SEQ ID NO 27
<211> LENGTH: 20
<212> TYPE: PRT
<213> ORGANISM: Artificial sequence
<220> FEATURE:
<223> OTHER INFORMATION: Linear peptide and D-peptide analogs

<400> SEQUENCE: 27

Phe Leu Leu Ser Trp Val His Trp Ser Leu Ala Leu Leu Leu Tyr Leu
1               5                   10                  15

His His Ala Lys
            20

<210> SEQ ID NO 28
<211> LENGTH: 18
<212> TYPE: PRT
<213> ORGANISM: Artificial sequence
<220> FEATURE:
<223> OTHER INFORMATION: Cyclic peptide and D-peptide analogs

<400> SEQUENCE: 28

Cys Val Pro Leu Met Arg Cys Gly Gly Cys Asn Asp Glu Gly Leu
1               5                   10                  15

Glu Cys

<210> SEQ ID NO 29
<211> LENGTH: 22
<212> TYPE: PRT
<213> ORGANISM: Artificial sequence
<220> FEATURE:
<223> OTHER INFORMATION: Cyclic peptide and D-peptide analogs

<400> SEQUENCE: 29

Cys Gly Pro Cys Ser Glu Arg Arg Lys His Leu Phe Val Gln Asp Pro
1               5                   10                  15

Gln Thr Cys Lys Cys Ser
            20

<210> SEQ ID NO 30
<211> LENGTH: 22
<212> TYPE: PRT
<213> ORGANISM: Artificial sequence
<220> FEATURE:
<223> OTHER INFORMATION: Cyclic peptide and D-peptide analogs

<400> SEQUENCE: 30

Cys Lys Asn Thr Asp Ser Arg Cys Lys Ala Arg Gln Leu Glu Leu Asn
1               5                   10                  15

Glu Arg Thr Cys Arg Cys
            20

<210> SEQ ID NO 31
<211> LENGTH: 16
<212> TYPE: PRT
<213> ORGANISM: Artificial sequence
<220> FEATURE:
<223> OTHER INFORMATION: Linear peptide and D-peptide analogs

<400> SEQUENCE: 31

His Ala Asn Arg Ile Tyr Arg Met Ile Lys Leu Gly Leu Gly Ile Asp
1               5                   10                  15

<210> SEQ ID NO 32
```

```
<211> LENGTH: 21
<212> TYPE: PRT
<213> ORGANISM: Artificial sequence
<220> FEATURE:
<223> OTHER INFORMATION: Linear peptide and D-peptide analogs

<400> SEQUENCE: 32

Lys Ile Met Lys Asp Ile Leu Glu Lys Lys Val Glu Lys Val Val Val
1               5                   10                  15

Ser Asn Arg Leu Val
            20

<210> SEQ ID NO 33
<211> LENGTH: 16
<212> TYPE: PRT
<213> ORGANISM: Artificial sequence
<220> FEATURE:
<223> OTHER INFORMATION: Linear peptide and D-peptide analogs

<400> SEQUENCE: 33

Gly Gln Phe Gly Val Gly Phe Tyr Ser Ala Tyr Leu Val Ala Glu Lys
1               5                   10                  15

<210> SEQ ID NO 34
<211> LENGTH: 7
<212> TYPE: PRT
<213> ORGANISM: Artificial sequence
<220> FEATURE:
<223> OTHER INFORMATION: Cyclic peptide and D-peptide analogs

<400> SEQUENCE: 34

Cys Met Glu Glu Val Asp Cys
1               5

<210> SEQ ID NO 35
<211> LENGTH: 13
<212> TYPE: PRT
<213> ORGANISM: Artificial sequence
<220> FEATURE:
<223> OTHER INFORMATION: Linear peptide and D-peptide analogs

<400> SEQUENCE: 35

Thr Thr Pro Ser Tyr Val Ala Phe Thr Asp Thr Glu Arg
1               5                   10

<210> SEQ ID NO 36
<211> LENGTH: 13
<212> TYPE: PRT
<213> ORGANISM: Artificial sequence
<220> FEATURE:
<223> OTHER INFORMATION: Linear peptide and D-peptide analogs

<400> SEQUENCE: 36

Lys Tyr Lys Ala Glu Asp Glu Val Gln Arg Glu Lys Ile
1               5                   10

<210> SEQ ID NO 37
<211> LENGTH: 10
<212> TYPE: PRT
<213> ORGANISM: Artificial sequence
<220> FEATURE:
<223> OTHER INFORMATION: Cyclic peptide and D-peptide analogs

<400> SEQUENCE: 37

Cys Gly Pro Thr Ile Glu Glu Val Asp Cys
1               5                   10
```

```
<210> SEQ ID NO 38
<211> LENGTH: 12
<212> TYPE: PRT
<213> ORGANISM: Artificial sequence
<220> FEATURE:
<223> OTHER INFORMATION: Linear peptide and D-peptide analogs

<400> SEQUENCE: 38

Ala Arg Phe Glu Glu Leu Asn Ala Asp Leu Phe Arg
1               5                   10

<210> SEQ ID NO 39
<211> LENGTH: 16
<212> TYPE: PRT
<213> ORGANISM: Artificial sequence
<220> FEATURE:
<223> OTHER INFORMATION: Linear peptide and D-peptide analogs

<400> SEQUENCE: 39

Ser Thr Ala Gly Asp Thr His Leu Gly Gly Glu Asp Phe Asp Asn Arg
1               5                   10                  15

<210> SEQ ID NO 40
<211> LENGTH: 14
<212> TYPE: PRT
<213> ORGANISM: Artificial sequence
<220> FEATURE:
<223> OTHER INFORMATION: Linear peptide and D-peptide analogs

<400> SEQUENCE: 40

Lys Leu Leu Gln Asp Phe Phe Asn Gly Lys Glu Leu Asn Lys
1               5                   10

<210> SEQ ID NO 41
<211> LENGTH: 15
<212> TYPE: PRT
<213> ORGANISM: Artificial sequence
<220> FEATURE:
<223> OTHER INFORMATION: Linear peptide and D-peptide analogs

<400> SEQUENCE: 41

Met Val Leu Thr Lys Met Lys Glu Ile Ala Glu Ala Tyr Leu Gly
1               5                   10                  15

<210> SEQ ID NO 42
<211> LENGTH: 16
<212> TYPE: PRT
<213> ORGANISM: Artificial sequence
<220> FEATURE:
<223> OTHER INFORMATION: Linear peptide and D-peptide analogs

<400> SEQUENCE: 42

Gln Ala Thr Lys Asp Ala Gly Val Ile Ala Gly Leu Asn Val Leu Arg
1               5                   10                  15

<210> SEQ ID NO 43
<211> LENGTH: 16
<212> TYPE: PRT
<213> ORGANISM: Artificial sequence
<220> FEATURE:
<223> OTHER INFORMATION: Linear peptide and D-peptide analogs

<400> SEQUENCE: 43

Asn Gln Val Ala Met Asn Pro Thr Asn Thr Val Phe Asp Ala Lys Arg
1               5                   10                  15

<210> SEQ ID NO 44
<211> LENGTH: 12
```

```
<212> TYPE: PRT
<213> ORGANISM: Artificial sequence
<220> FEATURE:
<223> OTHER INFORMATION: Linear peptide and D-peptide analogs

<400> SEQUENCE: 44

Arg Phe Asp Asp Ala Val Val Gln Ser Asp Met Lys
1               5                   10

<210> SEQ ID NO 45
<211> LENGTH: 5
<212> TYPE: PRT
<213> ORGANISM: Artificial sequence
<220> FEATURE:
<223> OTHER INFORMATION: Cyclic peptide and D-peptide analogs

<400> SEQUENCE: 45

Cys Leu Asp Val Cys
1               5

<210> SEQ ID NO 46
<211> LENGTH: 10
<212> TYPE: PRT
<213> ORGANISM: Artificial sequence
<220> FEATURE:
<223> OTHER INFORMATION: Linear peptide and D-peptide analogs

<400> SEQUENCE: 46

Met Val Asn His Phe Ile Ala Glu Phe Lys
1               5                   10

<210> SEQ ID NO 47
<211> LENGTH: 13
<212> TYPE: PRT
<213> ORGANISM: Artificial sequence
<220> FEATURE:
<223> OTHER INFORMATION: Linear peptide and D-peptide analogs

<400> SEQUENCE: 47

Arg Ile Met Ser Ser Ala Lys Arg Pro Leu Trp Leu Asn
1               5                   10

<210> SEQ ID NO 48
<211> LENGTH: 16
<212> TYPE: PRT
<213> ORGANISM: Artificial sequence
<220> FEATURE:
<223> OTHER INFORMATION: Linear peptide and D-peptide analogs

<400> SEQUENCE: 48

Gly Leu Ile Glu Val Val Arg Asn Ser His Thr Ile Met Gln Ile Gln
1               5                   10                  15

<210> SEQ ID NO 49
<211> LENGTH: 7
<212> TYPE: PRT
<213> ORGANISM: Artificial sequence
<220> FEATURE:
<223> OTHER INFORMATION: Linear peptide and D-peptide analogs

<400> SEQUENCE: 49

Ile Phe Lys Asn Gly Asp Asp
1               5

<210> SEQ ID NO 50
<211> LENGTH: 14
<212> TYPE: PRT
<213> ORGANISM: Artificial sequence
```

```
<220> FEATURE:
<223> OTHER INFORMATION: Linear peptide and D-peptide analogs

<400> SEQUENCE: 50

Gly Gln Leu Phe His Ile Asp Phe Gly His Phe Leu Asp His
1               5                   10

<210> SEQ ID NO 51
<211> LENGTH: 10
<212> TYPE: PRT
<213> ORGANISM: Artificial sequence
<220> FEATURE:
<223> OTHER INFORMATION: Linear peptide and D-peptide analogs

<400> SEQUENCE: 51

Asp Arg His Asn Ser Asn Ile Met Val Lys
1               5                   10

<210> SEQ ID NO 52
<211> LENGTH: 15
<212> TYPE: PRT
<213> ORGANISM: Artificial sequence
<220> FEATURE:
<223> OTHER INFORMATION: Linear peptide and D-peptide analogs

<400> SEQUENCE: 52

Glu Val Val Gly Arg Gly Ala Phe Gly Val Val Cys Lys Ala Lys
1               5                   10                  15

<210> SEQ ID NO 53
<211> LENGTH: 11
<212> TYPE: PRT
<213> ORGANISM: Artificial sequence
<220> FEATURE:
<223> OTHER INFORMATION: Linear peptide and D-peptide analogs

<400> SEQUENCE: 53

Arg Ala Lys Asp Val Ala Ile Lys Gln Ile Glu
1               5                   10

<210> SEQ ID NO 54
<211> LENGTH: 19
<212> TYPE: PRT
<213> ORGANISM: Artificial sequence
<220> FEATURE:
<223> OTHER INFORMATION: Linear peptide and D-peptide analogs

<400> SEQUENCE: 54

Asn Leu Leu Leu Val Ala Gly Gly Thr Val Leu Lys Ile Cys Asp Phe
1               5                   10                  15

Gly Thr Ala

<210> SEQ ID NO 55
<211> LENGTH: 9
<212> TYPE: PRT
<213> ORGANISM: Artificial sequence
<220> FEATURE:
<223> OTHER INFORMATION: Linear peptide and D-peptide analogs

<400> SEQUENCE: 55

Val Ile Thr Ser Lys Gln Arg Pro Arg
1               5

<210> SEQ ID NO 56
<211> LENGTH: 8
<212> TYPE: PRT
<213> ORGANISM: Artificial sequence
```

<220> FEATURE:
<223> OTHER INFORMATION: Linear peptide and D-peptide analogs

<400> SEQUENCE: 56

Phe Leu Leu Lys Gly His Glu Asp
1               5

<210> SEQ ID NO 57
<211> LENGTH: 5
<212> TYPE: PRT
<213> ORGANISM: Artificial sequence
<220> FEATURE:
<223> OTHER INFORMATION: Linear peptide and D-peptide analogs

<400> SEQUENCE: 57

Ser Asn Leu Met Leu
1               5

<210> SEQ ID NO 58
<211> LENGTH: 10
<212> TYPE: PRT
<213> ORGANISM: Artificial sequence
<220> FEATURE:
<223> OTHER INFORMATION: Cyclic peptide and D-peptide analogs

<400> SEQUENCE: 58

Cys Ile Gly Trp Val Pro His Cys Asp Thr
1               5                   10

<210> SEQ ID NO 59
<211> LENGTH: 15
<212> TYPE: PRT
<213> ORGANISM: Artificial sequence
<220> FEATURE:
<223> OTHER INFORMATION: Linear peptide and D-peptide analogs

<400> SEQUENCE: 59

Thr Gln Ala Trp Asp Leu Tyr Tyr His Val Phe Arg Arg Ile Ser
1               5                   10                  15

<210> SEQ ID NO 60
<211> LENGTH: 13
<212> TYPE: PRT
<213> ORGANISM: Artificial sequence
<220> FEATURE:
<223> OTHER INFORMATION: Linear peptide and D-peptide analogs

<400> SEQUENCE: 60

His Glu Gly Leu Glu Glu Ala Ser Arg Leu Tyr Phe Gly
1               5                   10

<210> SEQ ID NO 61
<211> LENGTH: 14
<212> TYPE: PRT
<213> ORGANISM: Artificial sequence
<220> FEATURE:
<223> OTHER INFORMATION: Linear peptide and D-peptide analogs

<400> SEQUENCE: 61

Arg Val Met Gln Leu Phe Gly Leu Val Asn Thr Leu Leu Ala
1               5                   10

<210> SEQ ID NO 62
<211> LENGTH: 13
<212> TYPE: PRT
<213> ORGANISM: Artificial sequence
<220> FEATURE:
<223> OTHER INFORMATION: Linear peptide and D-peptide analogs

```
<400> SEQUENCE: 62

Lys Ile Leu Leu Asn Ile Glu His Arg Ile Met Leu Arg
1               5                   10

<210> SEQ ID NO 63
<211> LENGTH: 9
<212> TYPE: PRT
<213> ORGANISM: Artificial sequence
<220> FEATURE:
<223> OTHER INFORMATION: Linear peptide and D-peptide analogs

<400> SEQUENCE: 63

Asp Leu Ala Lys Leu Leu Trp Leu Lys
1               5

<210> SEQ ID NO 64
<211> LENGTH: 13
<212> TYPE: PRT
<213> ORGANISM: Artificial sequence
<220> FEATURE:
<223> OTHER INFORMATION: Linear peptide and D-peptide analogs

<400> SEQUENCE: 64

Ser Leu Ala Val Met Ser Met Val Gly Tyr Ile Leu Gly
1               5                   10

<210> SEQ ID NO 65
<211> LENGTH: 16
<212> TYPE: PRT
<213> ORGANISM: Artificial sequence
<220> FEATURE:
<223> OTHER INFORMATION: Linear peptide and D-peptide analogs

<400> SEQUENCE: 65

Arg Leu Thr Arg Met Leu Thr Asn Ala Met Glu Val Thr Gly Leu Asp
1               5                   10                  15

<210> SEQ ID NO 66
<211> LENGTH: 8
<212> TYPE: PRT
<213> ORGANISM: Artificial sequence
<220> FEATURE:
<223> OTHER INFORMATION: Linear peptide and D-peptide analogs

<400> SEQUENCE: 66

His Thr Val Met Glu Val Leu Arg
1               5

<210> SEQ ID NO 67
<211> LENGTH: 10
<212> TYPE: PRT
<213> ORGANISM: Artificial sequence
<220> FEATURE:
<223> OTHER INFORMATION: Linear peptide and D-peptide analogs

<400> SEQUENCE: 67

Gly Arg Gly Ala Phe Gly Gln Val Ile Glu
1               5                   10

<210> SEQ ID NO 68
<211> LENGTH: 9
<212> TYPE: PRT
<213> ORGANISM: Artificial sequence
<220> FEATURE:
<223> OTHER INFORMATION: linear peptide and D-peptide analogs

<400> SEQUENCE: 68
```

```
Arg Thr Val Ala Val Lys Met Leu Lys
1               5
```

<210> SEQ ID NO 69
<211> LENGTH: 16
<212> TYPE: PRT
<213> ORGANISM: Artificial sequence
<220> FEATURE:
<223> OTHER INFORMATION: Linear peptide and D-peptide analogs

<400> SEQUENCE: 69

```
Val Ile Val Glu Phe Cys Lys Phe Gly Asn Leu Ser Thr Tyr Leu Arg
1               5                   10                  15
```

<210> SEQ ID NO 70
<211> LENGTH: 5
<212> TYPE: PRT
<213> ORGANISM: Artificial sequence
<220> FEATURE:
<223> OTHER INFORMATION: Cyclic peptide and D-peptide analogs

<400> SEQUENCE: 70

```
Cys Leu Asp Thr Cys
1               5
```

<210> SEQ ID NO 71
<211> LENGTH: 8
<212> TYPE: PRT
<213> ORGANISM: Artificial sequence
<220> FEATURE:
<223> OTHER INFORMATION: Linear peptide and D-peptide analogs

<400> SEQUENCE: 71

```
Gly Asp Ala Arg Leu Pro Leu Lys
1               5
```

<210> SEQ ID NO 72
<211> LENGTH: 11
<212> TYPE: PRT
<213> ORGANISM: Artificial sequence
<220> FEATURE:
<223> OTHER INFORMATION: Linear peptide and D-peptide analogs

<400> SEQUENCE: 72

```
Val Leu Gly Ser Gly Ala Phe Gly Lys Val Val
1               5                   10
```

<210> SEQ ID NO 73
<211> LENGTH: 10
<212> TYPE: PRT
<213> ORGANISM: Artificial sequence
<220> FEATURE:
<223> OTHER INFORMATION: Linear peptide and D-peptide analogs

<400> SEQUENCE: 73

```
Val Met Lys Val Ala Val Lys Met Leu Lys
1               5                   10
```

<210> SEQ ID NO 74
<211> LENGTH: 9
<212> TYPE: PRT
<213> ORGANISM: Artificial sequence
<220> FEATURE:
<223> OTHER INFORMATION: Linear peptide and D-peptide analogs

<400> SEQUENCE: 74

```
Ile Thr Glu Tyr Cys Phe Tyr Gly Asp
```

```
1               5

<210> SEQ ID NO 75
<211> LENGTH: 9
<212> TYPE: PRT
<213> ORGANISM: Artificial sequence
<220> FEATURE:
<223> OTHER INFORMATION: Linear peptide and D-peptide analogs

<400> SEQUENCE: 75

Arg Asp Leu Ala Ala Arg Asn Val Leu
1               5

<210> SEQ ID NO 76
<211> LENGTH: 11
<212> TYPE: PRT
<213> ORGANISM: Artificial sequence
<220> FEATURE:
<223> OTHER INFORMATION: Linear peptide and D-peptide analogs

<400> SEQUENCE: 76

Thr Met Lys Val Ala Val Lys Met Leu Lys Ser
1               5                   10

<210> SEQ ID NO 77
<211> LENGTH: 15
<212> TYPE: PRT
<213> ORGANISM: Artificial sequence
<220> FEATURE:
<223> OTHER INFORMATION: Linear peptide and D-peptide analogs

<400> SEQUENCE: 77

Arg Thr Leu Gly Ser Gly Ala Phe Gly Gln Val Val Glu Ala Thr
1               5                   10                  15

<210> SEQ ID NO 78
<211> LENGTH: 9
<212> TYPE: PRT
<213> ORGANISM: Artificial sequence
<220> FEATURE:
<223> OTHER INFORMATION: Linear peptide and D-peptide analogs

<400> SEQUENCE: 78

Ile Thr Glu Tyr Cys Arg Tyr Gly Asp
1               5

<210> SEQ ID NO 79
<211> LENGTH: 53
<212> TYPE: PRT
<213> ORGANISM: Artificial sequence
<220> FEATURE:
<223> OTHER INFORMATION: Cyclic peptide and D-peptide analogs

<400> SEQUENCE: 79

Cys Pro Asp Ser Gln Phe Glu Cys Pro Asp Phe Ser Thr Cys Val
1               5                   10                  15

Met Val Asp Gly Ser Trp Gly Cys Cys Pro Met Pro Gln Ala Ser Cys
                20                  25                  30

Cys Glu Asp Arg Val His Cys Cys Pro His Gly Ala Phe Cys Asp Leu
            35                  40                  45

Val His Thr Arg Cys
        50

<210> SEQ ID NO 80
<211> LENGTH: 24
<212> TYPE: PRT
```

```
<213> ORGANISM: Artificial sequence
<220> FEATURE:
<223> OTHER INFORMATION: Cyclic peptide and D-peptide analogs

<400> SEQUENCE: 80

Cys Pro Asp Ser Gln Phe Glu Cys Pro Asp Phe Ser Thr Cys Cys Val
1               5                   10                  15

Met Val Asp Gly Ser Trp Gly Cys
            20

<210> SEQ ID NO 81
<211> LENGTH: 29
<212> TYPE: PRT
<213> ORGANISM: Artificial sequence
<220> FEATURE:
<223> OTHER INFORMATION: Cyclic peptide and D-peptide analogs

<400> SEQUENCE: 81

Cys Pro Met Pro Gln Ala Ser Cys Cys Glu Asp Arg Val His Cys Cys
1               5                   10                  15

Pro His Gly Ala Phe Cys Asp Leu Val His Thr Arg Cys
            20                  25

<210> SEQ ID NO 82
<211> LENGTH: 18
<212> TYPE: PRT
<213> ORGANISM: Artificial sequence
<220> FEATURE:
<223> OTHER INFORMATION: Cyclic peptide and D-peptide analogs

<400> SEQUENCE: 82

Cys Val Met Val Asp Gly Ser Trp Gly Cys Cys Pro Met Pro Gln Ala
1               5                   10                  15

Ser Cys

<210> SEQ ID NO 83
<211> LENGTH: 21
<212> TYPE: PRT
<213> ORGANISM: Artificial sequence
<220> FEATURE:
<223> OTHER INFORMATION: Cyclic peptide and D-peptide analogs

<400> SEQUENCE: 83

Cys Glu Asp Arg Val His Cys Cys Pro His Gly Ala Phe Cys Asp Leu
1               5                   10                  15

Val His Thr Arg Cys
            20

<210> SEQ ID NO 84
<211> LENGTH: 52
<212> TYPE: PRT
<213> ORGANISM: Artificial sequence
<220> FEATURE:
<223> OTHER INFORMATION: Cyclic peptide and D-peptide analogs

<400> SEQUENCE: 84

Cys Asp Gln His Thr Ser Cys Pro Val Gly Gln Thr Cys Cys Pro Ser
1               5                   10                  15

Leu Gly Gly Ser Trp Ala Cys Cys Gln Leu Pro His Ala Val Cys Cys
            20                  25                  30

Glu Asp Arg Gln His Cys Cys Pro Ala Gly Tyr Thr Cys Asn Val Lys
        35                  40                  45

Ala Arg Ser Cys
    50
```

<210> SEQ ID NO 85
<211> LENGTH: 23
<212> TYPE: PRT
<213> ORGANISM: Artificial sequence
<220> FEATURE:
<223> OTHER INFORMATION: Cyclic peptide and D-peptide analogs

<400> SEQUENCE: 85

Cys Asp Gln His Thr Ser Cys Pro Val Gly Gln Thr Cys Cys Pro Ser
1               5                   10                  15

Leu Gly Gly Ser Trp Ala Cys
            20

<210> SEQ ID NO 86
<211> LENGTH: 29
<212> TYPE: PRT
<213> ORGANISM: Artificial sequence
<220> FEATURE:
<223> OTHER INFORMATION: Cyclic peptide and D-peptide analogs

<400> SEQUENCE: 86

Cys Gln Leu Pro His Ala Val Cys Cys Glu Asp Arg Gln His Cys Cys
1               5                   10                  15

Pro Ala Gly Tyr Thr Cys Asn Val Lys Ala Arg Ser Cys
            20                  25

<210> SEQ ID NO 87
<211> LENGTH: 18
<212> TYPE: PRT
<213> ORGANISM: Artificial sequence
<220> FEATURE:
<223> OTHER INFORMATION: Cyclic peptide and D-peptide analogs

<400> SEQUENCE: 87

Cys Pro Ser Leu Gly Gly Ser Trp Ala Cys Cys Gln Leu Pro His Ala
1               5                   10                  15

Val Cys

<210> SEQ ID NO 88
<211> LENGTH: 21
<212> TYPE: PRT
<213> ORGANISM: Artificial sequence
<220> FEATURE:
<223> OTHER INFORMATION: Cyclic peptide and D-peptide analogs

<400> SEQUENCE: 88

Cys Glu Asp Arg Gln His Cys Cys Pro Ala Gly Tyr Thr Cys Asn Val
1               5                   10                  15

Lys Ala Arg Ser Cys
            20

<210> SEQ ID NO 89
<211> LENGTH: 52
<212> TYPE: PRT
<213> ORGANISM: Artificial sequence
<220> FEATURE:
<223> OTHER INFORMATION: Cyclic peptide and D-peptide analogs

<400> SEQUENCE: 89

Cys Asp Met Glu Val Ser Cys Pro Asp Gly Tyr Thr Cys Cys Arg Leu
1               5                   10                  15

Gln Ser Gly Ala Trp Gly Cys Cys Pro Phe Thr Gln Ala Val Cys Cys
            20                  25                  30

-continued

```
Glu Asp His Ile His Cys Cys Pro Ala Gly Phe Thr Cys Asp Thr Gln
         35                  40                  45

Lys Gly Thr Cys
    50

<210> SEQ ID NO 90
<211> LENGTH: 23
<212> TYPE: PRT
<213> ORGANISM: Artificial sequence
<220> FEATURE:
<223> OTHER INFORMATION: Cyclic peptide and D-peptide analogs

<400> SEQUENCE: 90

Cys Asp Met Glu Val Ser Cys Pro Asp Gly Tyr Thr Cys Cys Arg Leu
1               5                   10                  15

Gln Ser Gly Ala Trp Gly Cys
            20

<210> SEQ ID NO 91
<211> LENGTH: 29
<212> TYPE: PRT
<213> ORGANISM: Artificial sequence
<220> FEATURE:
<223> OTHER INFORMATION: Cyclic peptide and D-peptide analogs

<400> SEQUENCE: 91

Cys Pro Phe Thr Gln Ala Val Cys Cys Glu Asp His Ile His Cys Cys
1               5                   10                  15

Pro Ala Gly Phe Thr Cys Asp Thr Gln Lys Gly Thr Cys
            20                  25

<210> SEQ ID NO 92
<211> LENGTH: 18
<212> TYPE: PRT
<213> ORGANISM: Artificial sequence
<220> FEATURE:
<223> OTHER INFORMATION: Cyclic peptide and D-peptide analogs

<400> SEQUENCE: 92

Cys Arg Leu Gln Ser Gly Ala Trp Gly Cys Cys Pro Phe Thr Gln Ala
1               5                   10                  15

Val Cys

<210> SEQ ID NO 93
<211> LENGTH: 21
<212> TYPE: PRT
<213> ORGANISM: Artificial sequence
<220> FEATURE:
<223> OTHER INFORMATION: Cyclic peptide and D-peptide analogs

<400> SEQUENCE: 93

Cys Glu Asp His Ile His Cys Cys Pro Ala Gly Phe Thr Cys Asp Thr
1               5                   10                  15

Gln Lys Gly Thr Cys
            20

<210> SEQ ID NO 94
<211> LENGTH: 28
<212> TYPE: PRT
<213> ORGANISM: Artificial sequence
<220> FEATURE:
<223> OTHER INFORMATION: Cyclic peptide and D-peptide analogs

<400> SEQUENCE: 94

Cys Gly Gly Arg Leu Asn Ser Lys Asp Ala Gly Tyr Ile Thr Ser Pro
```

```
1               5                   10                  15

Gly Tyr Pro Gln Asp Tyr Pro Ser His Gln Asn Cys
            20                  25

<210> SEQ ID NO 95
<211> LENGTH: 27
<212> TYPE: PRT
<213> ORGANISM: Artificial sequence
<220> FEATURE:
<223> OTHER INFORMATION: Cyclic peptide and D-peptide analogs

<400> SEQUENCE: 95

Cys Ser Lys Asn Phe Thr Ser Pro Asn Gly Thr Ile Glu Ser Pro Gly
1               5                   10                  15

Phe Pro Glu Lys Tyr Pro His Asn Leu Asp Cys
            20                  25

<210> SEQ ID NO 96
<211> LENGTH: 23
<212> TYPE: PRT
<213> ORGANISM: Artificial sequence
<220> FEATURE:
<223> OTHER INFORMATION: Cyclic peptide and D-peptide analogs

<400> SEQUENCE: 96

Cys Lys Tyr Asp Trp Leu Asp Ile Trp Asp Gly Ile Pro His Val Gly
1               5                   10                  15

Pro Leu Ile Gly Lys Tyr Cys
            20

<210> SEQ ID NO 97
<211> LENGTH: 7
<212> TYPE: PRT
<213> ORGANISM: Artificial sequence
<220> FEATURE:
<223> OTHER INFORMATION: Cyclic peptide and D-peptide analogs

<400> SEQUENCE: 97

Cys Trp Leu Asp Ile Trp Cys
1               5

<210> SEQ ID NO 98
<211> LENGTH: 10
<212> TYPE: PRT
<213> ORGANISM: Artificial sequence
<220> FEATURE:
<223> OTHER INFORMATION: Cyclic peptide and D-peptide analogs

<400> SEQUENCE: 98

Cys Asn Gly Trp Thr Pro Asn Leu Asp Cys
1               5                   10

<210> SEQ ID NO 99
<211> LENGTH: 14
<212> TYPE: PRT
<213> ORGANISM: Artificial sequence
<220> FEATURE:
<223> OTHER INFORMATION: Cyclic peptide and D-peptide analogs

<400> SEQUENCE: 99

Cys Arg Ser Gln Asp Ile Asp Ala Asp Gly Gln Gly Phe Cys
1               5                   10

<210> SEQ ID NO 100
<211> LENGTH: 11
<212> TYPE: PRT
```

```
<213> ORGANISM: Artificial sequence
<220> FEATURE:
<223> OTHER INFORMATION: Linear peptide and D-peptide analogs

<400> SEQUENCE: 100

Met Asp Leu Ser Tyr Ser Met Lys Asp Leu
1               5                   10

<210> SEQ ID NO 101
<211> LENGTH: 7
<212> TYPE: PRT
<213> ORGANISM: Artificial sequence
<220> FEATURE:
<223> OTHER INFORMATION: Cyclic peptide and D-peptide analogs

<400> SEQUENCE: 101

Cys Leu Leu Asp Thr Gly Cys
1               5

<210> SEQ ID NO 102
<211> LENGTH: 14
<212> TYPE: PRT
<213> ORGANISM: Artificial sequence
<220> FEATURE:
<223> OTHER INFORMATION: Linear peptide and D-peptide analogs

<400> SEQUENCE: 102

His Leu Leu Val Phe Thr Thr Asp Ala Lys Thr His Ile Ala
1               5                   10

<210> SEQ ID NO 103
<211> LENGTH: 8
<212> TYPE: PRT
<213> ORGANISM: Artificial sequence
<220> FEATURE:
<223> OTHER INFORMATION: Cyclic peptide and D-peptide analogs

<400> SEQUENCE: 103

Cys Tyr Asp Met Lys Thr Thr Cys
1               5

<210> SEQ ID NO 104
<211> LENGTH: 13
<212> TYPE: PRT
<213> ORGANISM: Artificial sequence
<220> FEATURE:
<223> OTHER INFORMATION: Cyclic peptide and D-peptide analogs

<400> SEQUENCE: 104

Cys Leu Asn Asn Glu Val Ile Pro Gly Leu Lys Ser Cys
1               5                   10

<210> SEQ ID NO 105
<211> LENGTH: 25
<212> TYPE: PRT
<213> ORGANISM: Artificial sequence
<220> FEATURE:
<223> OTHER INFORMATION: Cyclic peptide and D-peptide analogs

<400> SEQUENCE: 105

Cys Cys Phe Ala Tyr Ile Ala Arg Pro Leu Pro Arg Ala His Ile Lys
1               5                   10                  15

Glu Tyr Phe Tyr Thr Ser Gly Lys Cys
            20                  25

<210> SEQ ID NO 106
<211> LENGTH: 41
```

```
<212> TYPE: PRT
<213> ORGANISM: Artificial sequence
<220> FEATURE:
<223> OTHER INFORMATION: Cyclic peptide and D-peptide analogs

<400> SEQUENCE: 106

Cys Cys Phe Ala Tyr Ile Ala Arg Pro Leu Pro Arg Ala His Ile Lys
1               5                   10                  15

Glu Tyr Phe Tyr Thr Ser Gly Lys Cys Ser Asn Pro Ala Val Val Phe
            20                  25                  30

Val Thr Arg Lys Asn Arg Gln Val Cys
        35                  40

<210> SEQ ID NO 107
<211> LENGTH: 7
<212> TYPE: PRT
<213> ORGANISM: Artificial sequence
<220> FEATURE:
<223> OTHER INFORMATION: Cyclic peptide and D-peptide analogs

<400> SEQUENCE: 107

Cys Ser Leu Leu Gly Ile Cys
1               5

<210> SEQ ID NO 108
<211> LENGTH: 12
<212> TYPE: PRT
<213> ORGANISM: Artificial sequence
<220> FEATURE:
<223> OTHER INFORMATION: Linear peptide and D-peptide analogs

<400> SEQUENCE: 108

Arg Phe Ile Val Val Val Lys Ala Thr Lys Ala Tyr
1               5                   10

<210> SEQ ID NO 109
<211> LENGTH: 14
<212> TYPE: PRT
<213> ORGANISM: Artificial sequence
<220> FEATURE:
<223> OTHER INFORMATION: Linear peptide and D-peptide analogs

<400> SEQUENCE: 109

Thr Trp Gly Lys Val Thr Ser Leu Leu Ile Trp Val Ile Ser
1               5                   10

<210> SEQ ID NO 110
<211> LENGTH: 12
<212> TYPE: PRT
<213> ORGANISM: Artificial sequence
<220> FEATURE:
<223> OTHER INFORMATION: Linear peptide and D-peptide analogs

<400> SEQUENCE: 110

Arg Arg Leu Arg Ile Met Thr Asn Ile Tyr Leu Leu
1               5                   10

<210> SEQ ID NO 111
<211> LENGTH: 13
<212> TYPE: PRT
<213> ORGANISM: Artificial sequence
<220> FEATURE:
<223> OTHER INFORMATION: Cyclic peptide and D-peptide analogs

<400> SEQUENCE: 111

Cys Asn Lys Cys Tyr Cys Lys Lys Cys Cys Tyr His Cys
1               5                   10
```

-continued

```
<210> SEQ ID NO 112
<211> LENGTH: 7
<212> TYPE: PRT
<213> ORGANISM: Artificial sequence
<220> FEATURE:
<223> OTHER INFORMATION: Cyclic peptide and D-peptide analogs

<400> SEQUENCE: 112

Cys Pro Arg Gly Asp Pro Cys
1               5

<210> SEQ ID NO 113
<211> LENGTH: 7
<212> TYPE: PRT
<213> ORGANISM: Artificial sequence
<220> FEATURE:
<223> OTHER INFORMATION: Cyclic peptide and D-peptide analogs

<400> SEQUENCE: 113

Cys Val Leu Asp Val Gly Cys
1               5

<210> SEQ ID NO 114
<211> LENGTH: 31
<212> TYPE: PRT
<213> ORGANISM: Artificial sequence
<220> FEATURE:
<223> OTHER INFORMATION: Cyclic peptide and D-peptide analogs

<400> SEQUENCE: 114

Cys Glu Thr Trp Arg Thr Glu Ala Pro Ser Ala Thr Gly Gln Ala Ser
1               5                   10                  15

Ser Leu Leu Gly Gly Arg Leu Leu Gly Gln Ser Ala Ala Ser Cys
            20                  25                  30

<210> SEQ ID NO 115
<211> LENGTH: 6
<212> TYPE: PRT
<213> ORGANISM: Artificial sequence
<220> FEATURE:
<223> OTHER INFORMATION: Cyclic peptide and D-peptide analogs

<400> SEQUENCE: 115

Cys Ser Val Thr Cys Gly
1               5

<210> SEQ ID NO 116
<211> LENGTH: 12
<212> TYPE: PRT
<213> ORGANISM: Artificial sequence
<220> FEATURE:
<223> OTHER INFORMATION: Cyclic peptide and D-peptide analogs

<400> SEQUENCE: 116

Cys Lys Asp Asn Lys Phe Asn Gly Lys Gly Pro Cys
1               5                   10

<210> SEQ ID NO 117
<211> LENGTH: 20
<212> TYPE: PRT
<213> ORGANISM: Artificial sequence
<220> FEATURE:
<223> OTHER INFORMATION: Linear peptide and D-peptide analogs

<400> SEQUENCE: 117

Gln His Leu Leu Gln Leu Thr Val Trp Gly Ile Lys Gln Leu Gln Ala
```

```
1               5                  10                 15
Arg Ile Leu Ala
            20

<210> SEQ ID NO 118
<211> LENGTH: 11
<212> TYPE: PRT
<213> ORGANISM: Artificial sequence
<220> FEATURE:
<223> OTHER INFORMATION: Linear peptide and D-peptide analogs

<400> SEQUENCE: 118

Asn Val Ser Tyr Ile Cys Ser Arg Tyr Tyr Arg
1               5                  10

<210> SEQ ID NO 119
<211> LENGTH: 10
<212> TYPE: PRT
<213> ORGANISM: Artificial sequence
<220> FEATURE:
<223> OTHER INFORMATION: Linear peptide and D-peptide analogs

<400> SEQUENCE: 119

His Arg Asp Ile Lys Pro Gln Asn Leu Leu
1               5                  10

<210> SEQ ID NO 120
<211> LENGTH: 7
<212> TYPE: PRT
<213> ORGANISM: Artificial sequence
<220> FEATURE:
<223> OTHER INFORMATION: Cyclic peptide and D-peptide analogs

<400> SEQUENCE: 120

Cys Arg Leu Leu Gly Gln Cys
1               5

<210> SEQ ID NO 121
<211> LENGTH: 10
<212> TYPE: PRT
<213> ORGANISM: Artificial sequence
<220> FEATURE:
<223> OTHER INFORMATION: Linear peptide and D-peptide analogs

<400> SEQUENCE: 121

Val Ile Gly Asn Gly Ser Phe Gly Val Val
1               5                  10

<210> SEQ ID NO 122
<211> LENGTH: 36
<212> TYPE: PRT
<213> ORGANISM: Artificial sequence
<220> FEATURE:
<223> OTHER INFORMATION: Cyclic peptide and D-peptide analogs

<400> SEQUENCE: 122

Cys Val Asn Ile Thr Ile Lys Gln His Thr Val Thr Thr Thr Thr Lys
1               5                  10                 15

Gly Glu Asn Phe Thr Glu Thr Asp Val Lys Met Met Glu Arg Val Val
            20                 25                 30

Glu Gln Met Cys
        35

<210> SEQ ID NO 123
<211> LENGTH: 12
<212> TYPE: PRT
```

```
<213> ORGANISM: Artificial sequence
<220> FEATURE:
<223> OTHER INFORMATION: Linear peptide and D-peptide analogs

<400> SEQUENCE: 123

Tyr Arg Gly Tyr Arg Gly Tyr Arg Gly Tyr Arg Gly
1               5                   10

<210> SEQ ID NO 124
<211> LENGTH: 8
<212> TYPE: PRT
<213> ORGANISM: Artificial sequence
<220> FEATURE:
<223> OTHER INFORMATION: Linear peptide and D-peptide analogs

<400> SEQUENCE: 124

Arg Tyr Arg Tyr Arg Tyr Arg Tyr
1               5

<210> SEQ ID NO 125
<211> LENGTH: 8
<212> TYPE: PRT
<213> ORGANISM: Artificial sequence
<220> FEATURE:
<223> OTHER INFORMATION: Linear peptide and D-peptide analogs

<400> SEQUENCE: 125

Glu Ala Tyr Glu Met Pro Ser Glu
1               5

<210> SEQ ID NO 126
<211> LENGTH: 12
<212> TYPE: PRT
<213> ORGANISM: Artificial sequence
<220> FEATURE:
<223> OTHER INFORMATION: Linear peptide and D-peptide analogs

<400> SEQUENCE: 126

Gly Val Val His Gly Val Ala Thr Val Ala Glu Lys
1               5                   10

<210> SEQ ID NO 127
<211> LENGTH: 17
<212> TYPE: PRT
<213> ORGANISM: Artificial sequence
<220> FEATURE:
<223> OTHER INFORMATION: Cyclic peptide and D-peptide analogs

<400> SEQUENCE: 127

Cys Pro Gly Ala Cys Val Cys Tyr Asn Glu Pro Lys Val Thr Thr Ser
1               5                   10                  15

Cys

<210> SEQ ID NO 128
<211> LENGTH: 10
<212> TYPE: PRT
<213> ORGANISM: Artificial sequence
<220> FEATURE:
<223> OTHER INFORMATION: Linear peptide and D-peptide analogs

<400> SEQUENCE: 128

Arg Asn Leu Thr Ile Leu Trp Leu His Ser
1               5                   10

<210> SEQ ID NO 129
<211> LENGTH: 8
<212> TYPE: PRT
```

```
<213> ORGANISM: Artificial sequence
<220> FEATURE:
<223> OTHER INFORMATION: Linear peptide and D-peptide analogs

<400> SEQUENCE: 129

Thr His Leu Phe Leu His Gly Asn
1               5

<210> SEQ ID NO 130
<211> LENGTH: 24
<212> TYPE: PRT
<213> ORGANISM: Artificial sequence
<220> FEATURE:
<223> OTHER INFORMATION: Cyclic peptide and D-peptide analogs

<400> SEQUENCE: 130

Cys Asp Cys Arg Ala Arg Pro Leu Trp Ala Trp Leu Gln Lys Phe Arg
1               5                   10                  15

Gly Ser Ser Ser Glu Val Pro Cys
            20

<210> SEQ ID NO 131
<211> LENGTH: 11
<212> TYPE: PRT
<213> ORGANISM: Artificial sequence
<220> FEATURE:
<223> OTHER INFORMATION: Linear peptide and D-peptide analogs

<400> SEQUENCE: 131

Phe Leu Gly Ala Ala Gly Ser Thr Met Gly Ala
1               5                   10

<210> SEQ ID NO 132
<211> LENGTH: 11
<212> TYPE: PRT
<213> ORGANISM: Artificial sequence
<220> FEATURE:
<223> OTHER INFORMATION: Linear peptide and D-peptide analogs

<400> SEQUENCE: 132

Phe Leu Leu Lys Leu Ala Gly Arg Trp Pro Val
1               5                   10

<210> SEQ ID NO 133
<211> LENGTH: 9
<212> TYPE: PRT
<213> ORGANISM: Artificial sequence
<220> FEATURE:
<223> OTHER INFORMATION: Linear peptide and D-peptide analogs

<400> SEQUENCE: 133

Ile Val Gly Ala Glu Thr Phe Tyr Val
1               5

<210> SEQ ID NO 134
<211> LENGTH: 11
<212> TYPE: PRT
<213> ORGANISM: Artificial sequence
<220> FEATURE:
<223> OTHER INFORMATION: Linear peptide and D-peptide analogs

<400> SEQUENCE: 134

Ala Leu Leu Asp Thr Gly Ala Asp Asp Thr Val
1               5                   10

<210> SEQ ID NO 135
<211> LENGTH: 16
```

```
<212> TYPE: PRT
<213> ORGANISM: Artificial sequence
<220> FEATURE:
<223> OTHER INFORMATION: Linear peptide and D-peptide analogs

<400> SEQUENCE: 135

Ala His Lys Leu Gly Ser Gly Ala Tyr Gly Glu Val Leu Leu Cys Arg
1               5                   10                  15

<210> SEQ ID NO 136
<211> LENGTH: 12
<212> TYPE: PRT
<213> ORGANISM: Artificial sequence
<220> FEATURE:
<223> OTHER INFORMATION: Linear peptide and D-peptide analogs

<400> SEQUENCE: 136

Lys Leu Arg Asp Arg Leu Gly Thr Ala Tyr Tyr Ile
1               5                   10

<210> SEQ ID NO 137
<211> LENGTH: 10
<212> TYPE: PRT
<213> ORGANISM: Artificial sequence
<220> FEATURE:
<223> OTHER INFORMATION: Linear peptide and D-peptide analogs

<400> SEQUENCE: 137

Arg Leu Arg Asp Ala Phe Asn Leu Phe Asp
1               5                   10

<210> SEQ ID NO 138
<211> LENGTH: 22
<212> TYPE: PRT
<213> ORGANISM: Artificial sequence
<220> FEATURE:
<223> OTHER INFORMATION: Linear peptide and D-peptide analogs

<400> SEQUENCE: 138

Asn Lys Ala Val Met Asp Leu Lys Tyr His Leu Gln Lys Val Tyr Ala
1               5                   10                  15

Asn Tyr Leu Ser Gln Glu
            20

<210> SEQ ID NO 139
<211> LENGTH: 11
<212> TYPE: PRT
<213> ORGANISM: Artificial sequence
<220> FEATURE:
<223> OTHER INFORMATION: Linear peptide and D-peptide analogs

<400> SEQUENCE: 139

Phe Ile Ile Gly Gly Ser Val Val Tyr Gln Glu
1               5                   10

<210> SEQ ID NO 140
<211> LENGTH: 10
<212> TYPE: PRT
<213> ORGANISM: Artificial sequence
<220> FEATURE:
<223> OTHER INFORMATION: Cyclic peptide and D-peptide analogs

<400> SEQUENCE: 140

Cys Asn Ser Leu Asp Met Lys Tyr Phe Cys
1               5                   10

<210> SEQ ID NO 141
```

```
<211> LENGTH: 13
<212> TYPE: PRT
<213> ORGANISM: Artificial sequence
<220> FEATURE:
<223> OTHER INFORMATION: Linear peptide and D-peptide analogs

<400> SEQUENCE: 141

Ser Trp Glu Ser Ile Pro Lys Lys Phe Lys Pro Leu Ser
1               5                   10

<210> SEQ ID NO 142
<211> LENGTH: 20
<212> TYPE: PRT
<213> ORGANISM: Artificial sequence
<220> FEATURE:
<223> OTHER INFORMATION: Cyclic peptide and D-peptide analogs

<400> SEQUENCE: 142

Cys Cys Phe Cys Leu Pro Gly Gly Gly Val Cys Cys Leu Cys Ser
1               5                   10                  15

Glu Cys Ile Cys
            20

<210> SEQ ID NO 143
<211> LENGTH: 20
<212> TYPE: PRT
<213> ORGANISM: Artificial sequence
<220> FEATURE:
<223> OTHER INFORMATION: Linear peptide and D-peptide analogs

<400> SEQUENCE: 143

Arg Ala Leu Gln Val Val Arg Ala Arg Lys Gln Ile Val Ala Gly Val
1               5                   10                  15

Asn Tyr Phe Leu
            20

<210> SEQ ID NO 144
<211> LENGTH: 15
<212> TYPE: PRT
<213> ORGANISM: Artificial sequence
<220> FEATURE:
<223> OTHER INFORMATION: Cyclic peptide and D-peptide analogs

<400> SEQUENCE: 144

Cys Val Lys Gln Cys Cys Val Cys Cys Lys Gly Lys Asn Gly Cys
1               5                   10                  15

<210> SEQ ID NO 145
<211> LENGTH: 21
<212> TYPE: PRT
<213> ORGANISM: Artificial sequence
<220> FEATURE:
<223> OTHER INFORMATION: Cyclic peptide and D-peptide analogs

<400> SEQUENCE: 145

Cys Arg Gln Val Cys Pro Lys Ala Thr Arg Phe Val Cys Val Cys Cys
1               5                   10                  15

Lys Lys Ser Asp Cys
            20

<210> SEQ ID NO 146
<211> LENGTH: 17
<212> TYPE: PRT
<213> ORGANISM: Artificial sequence
<220> FEATURE:
<223> OTHER INFORMATION: Cyclic peptide and D-peptide analogs
```

-continued

```
<400> SEQUENCE: 146

Cys Arg Asp Asp Ser Glu Cys Ile Thr Arg Leu Cys Arg Lys Arg Arg
1               5                   10                  15

Cys

<210> SEQ ID NO 147
<211> LENGTH: 18
<212> TYPE: PRT
<213> ORGANISM: Artificial sequence
<220> FEATURE:
<223> OTHER INFORMATION: Cyclic peptide and D-peptide analogs

<400> SEQUENCE: 147

Arg Cys Ile Cys Thr Arg Gly Phe Cys Arg Cys Leu Cys Arg Arg Gly
1               5                   10                  15

Val Cys

<210> SEQ ID NO 148
<211> LENGTH: 18
<212> TYPE: PRT
<213> ORGANISM: Artificial sequence
<220> FEATURE:
<223> OTHER INFORMATION: Cyclic peptide and D-peptide analogs

<400> SEQUENCE: 148

Arg Cys Ile Cys Gly Arg Gly Ile Cys Arg Cys Ile Cys Gly Arg Gly
1               5                   10                  15

Ile Cys

<210> SEQ ID NO 149
<211> LENGTH: 15
<212> TYPE: PRT
<213> ORGANISM: Artificial sequence
<220> FEATURE:
<223> OTHER INFORMATION: Linear peptide and D-peptide analogs

<400> SEQUENCE: 149

Leu Ala Ala Arg Trp Ala Ala Lys Glu Ala Val Lys Ala Trp Ser
1               5                   10                  15

<210> SEQ ID NO 150
<211> LENGTH: 12
<212> TYPE: PRT
<213> ORGANISM: Artificial sequence
<220> FEATURE:
<223> OTHER INFORMATION: Linear peptide and D-peptide analogs

<400> SEQUENCE: 150

Val Pro Thr Met Gly Ala Leu His Glu Gly His Leu
1               5                   10

<210> SEQ ID NO 151
<211> LENGTH: 9
<212> TYPE: PRT
<213> ORGANISM: Artificial sequence
<220> FEATURE:
<223> OTHER INFORMATION: Linear peptide and D-peptide analogs

<400> SEQUENCE: 151

Ala Gly Val Leu Thr Val Val Leu Lys
1               5

<210> SEQ ID NO 152
<211> LENGTH: 12
<212> TYPE: PRT
```

```
<213> ORGANISM: Artificial sequence
<220> FEATURE:
<223> OTHER INFORMATION: Cyclic peptide and D-peptide analogs

<400> SEQUENCE: 152

Cys Phe Phe Gly Glu Lys Asp Tyr Gln Gln Leu Cys
1               5                   10
```